United States Patent
Nakaishi et al.

(10) Patent No.: US 11,155,833 B2
(45) Date of Patent: Oct. 26, 2021

(54) METHOD FOR PRODUCING TRANSGENIC CELL

(71) Applicant: KANEKA CORPORATION, Osaka (JP)

(72) Inventors: Tomoyuki Nakaishi, Hyogo (JP); Tatsuya Moutai, Hyogo (JP); Hiroshi Kita, Hyogo (JP); Mitsuaki Kitano, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 209 days.

(21) Appl. No.: 16/349,151

(22) PCT Filed: Nov. 10, 2017

(86) PCT No.: PCT/JP2017/040578
§ 371 (c)(1),
(2) Date: May 10, 2019

(87) PCT Pub. No.: WO2018/088519
PCT Pub. Date: May 17, 2018

(65) Prior Publication Data
US 2019/0271006 A1   Sep. 5, 2019

(30) Foreign Application Priority Data

Nov. 10, 2016 (JP) .............................. JP2016-219575

(51) Int. Cl.

| | |
|---|---|
| *C12N 15/86* | (2006.01) |
| *C07K 14/145* | (2006.01) |
| *C07K 16/28* | (2006.01) |
| *C12N 5/0735* | (2010.01) |
| *C12N 5/0781* | (2010.01) |
| *C12N 5/0783* | (2010.01) |
| *C12N 5/0775* | (2010.01) |
| *C12N 5/074* | (2010.01) |
| *C12N 7/00* | (2006.01) |
| *C12N 5/10* | (2006.01) |
| *A61K 48/00* | (2006.01) |
| *C12N 15/09* | (2006.01) |
| *A61K 35/76* | (2015.01) |
| *C07K 19/00* | (2006.01) |

(52) U.S. Cl.
CPC .............. *C12N 15/86* (2013.01); *A61K 35/76* (2013.01); *A61K 48/00* (2013.01); *C07K 14/145* (2013.01); *C07K 16/28* (2013.01); *C07K 19/00* (2013.01); *C12N 5/0606* (2013.01); *C12N 5/0635* (2013.01); *C12N 5/0636* (2013.01); *C12N 5/0663* (2013.01); *C12N 5/0696* (2013.01); *C12N 5/10* (2013.01); *C12N 7/00* (2013.01); *C12N 15/09* (2013.01); *C12N 2510/00* (2013.01); *C12N 2740/15043* (2013.01)

(58) Field of Classification Search
None
See application file for complete search history.

(56) References Cited

FOREIGN PATENT DOCUMENTS

| CN | 103865890 A | 6/2014 |
|---|---|---|
| JP | 2002516570 A | 6/2002 |
| WO | 9844132 A1 | 10/1998 |
| WO | 2011118699 A1 | 9/2011 |
| WO | 2012133349 A1 | 10/2012 |

OTHER PUBLICATIONS

Kameyama et al. J of Virological Methods 2008, vol. 153, pp. 49-54 (Year: 2008).*
Le Brun et al. Int. J. Mol. Sci. 2011, 12(8), 5157-5167 (Year: 2011).*
Hofig et al. Biomaterials vol. 35, Issue 13, pp. 4204-4212 (Year: 2014).*
BD Bioscience CD Marker Handbook 2010 (Year: 2010).*
Hartmann Blood 2003 vol. 101, pp. 2430-2431 (Year: 2003).*
Dominici et al. Cytotherapy 2006, vol. 8 pp. 315-317 (Year: 2006).*
Rodrigo et al., Antibodies vol. 4, pp. 259-277 (Year: 2015).*
Y. Kameyama et al., "Antibody-dependent gene transduction using gammaretroviral and lentiviral vectors pseudotyped with chimeric vesicular stomatitis virus glycoprotein," Journal of virological methods, 2008, vol. 153, pp. 49-54, abstract, materials and methods, fig. 1, 5, etc. (6 pages).
SCEJ 73rd Annual Meeting (Hamamatsu, 2008), 2008, I314, entire text, non-official translation (Kameyama, Yujiro, et al., "Transgenics using antibody-dependent virus vector by modification of envelope") (4 pages).
SCEJ 39th Autumn Meeting (Sapporo, 2007), 2007, 30F054, entire text, non-official translation (Kameyama, Yujiro, et al., "Development of specific antibody-dependent retrovirus vector system") (4 pages).
A. P. Le Brun et al., "Self-Assembly of Protein Monolayers Engineered for Improved Monoclonal Immonoglobulin G Binding," International Journal of Molecular Sciences, vol. 12, 2011, pp. 5157-5167, ISSN 1422-0067, abstract, fig. 1, 4, etc. (11 pages).
G. Rodrigo et al., "Antibody Fragments and Their Purification by Protein L Affinity Chromatography," Antibodies, 2015, vol. 4, pp. 259-277, ISSN 2073-4468, table 1, etc. (19 pages).

(Continued)

*Primary Examiner* — Shanon A. Foley
*Assistant Examiner* — Myron G Hill
(74) *Attorney, Agent, or Firm* — Osha Bergman Watanabe & Burton LLP

(57) ABSTRACT

A method for producing a transgenic cell, may include contacting, in vitro, (i) a virus comprising: a chimeric protein of an antibody-binding protein and a vesicular stomatitis virus G (VSV-G) protein; and a foreign gene, with (ii) a target cell and an antibody specific to the target cell, and/or a target cell comprising a membrane antibody, to infect the target cell with the virus.

17 Claims, 12 Drawing Sheets
Specification includes a Sequence Listing.

(56) References Cited

OTHER PUBLICATIONS

I. Höfig et al., "Systematic improvement of lentivirus transduction protocols by antibody fragments fused to VSV-G as envelope glycoprotein," Biomaterials, 2014, vol. 35, pp. 4204-4212, abstract (9 pages).

BD Biosciences, Human and Mouse CD Marker Handbook, [online] <https://www.bdbiosciences.com/documents/cd_marker_handbook.pdf>, 2010, [retrieved on Jan. 29, 2018], p. 3 (47 pages).

T. Matsushita et al., "The role of BAFF in autoimmune diseases," Japanese Journal of Clinical Immunology, 2005, vol. 28, No. 5, pp. 333-342, p. 336, right column, paragraph [0002] (10 pages).

G. Hartmann, "CpG: unraveling the key to B-cell function," BLOOD, Jun. 1, 2003, vol. 101, No. 11, pp. 4230-4231, paragraph [0001] (2 pages).

M. Dominici et al., "Minimal criteria for defining multipotent mesenchymal stromal cells. The International Society for Cellular Therapy position statement," Cytotherapy, 2006, vol. 8, No. 4, pp. 315-317, abstract (3 pages).

S. Froelich et al., "Pseudotyping Lentiviral Vectors with Aura Virus Envelope Glycoproteins for DC-SIGN-Mediated Transduction of Dendritic Cells," Human Gene Therapy, vol. 22, Oct. 2011, pp. 1281-1291 (11 pages).

International Search Report issued in corresponding International Application No. PCT/JP2017/040578; dated Feb. 6, 2018 (8 pages).

Written Opinion of the International Searching Authority issued in corresponding International Application No. PCT/JP2017/040578; dated Feb. 6, 2018 (21 pages).

International Preliminary Report on Patenability issued in corresponding International Application No. PCT/JP2017/040578; dated May 14, 2019 (11 pages).

K. Ojala et al., "Improved Display of Synthetic IgG-Binding Domains on the Baculovirus Surface"; Technology in Cancer Research & Treatment; vol. 3, No. 1, pp. 77-84; Feb. 1, 2004 (9 pages).

Extended European Search Report issued in corresponding European Application No. 17868965.9, dated May 8, 2020 (9 pages).

\* cited by examiner

[Fig. 1]
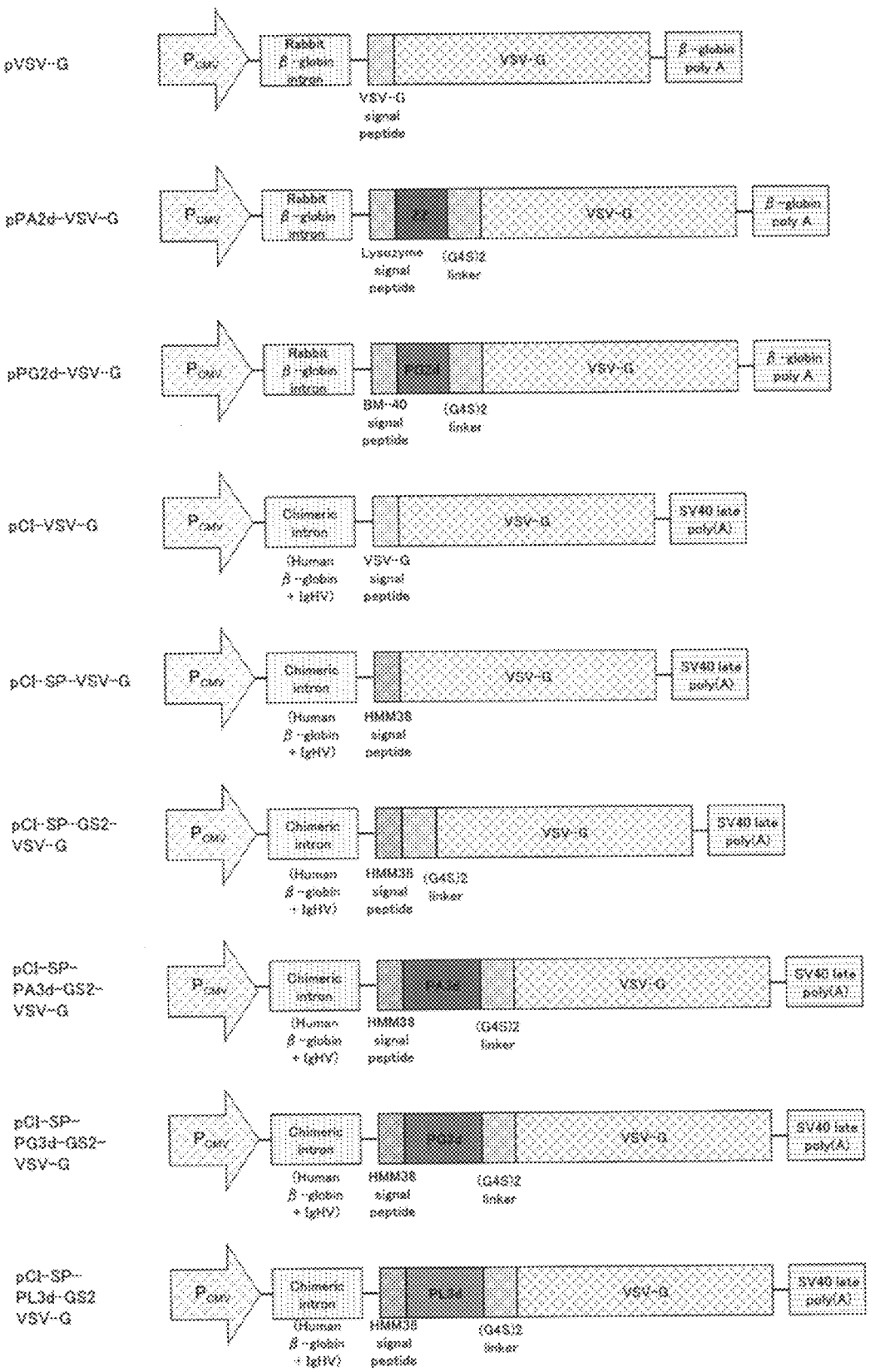

[Fig. 2]
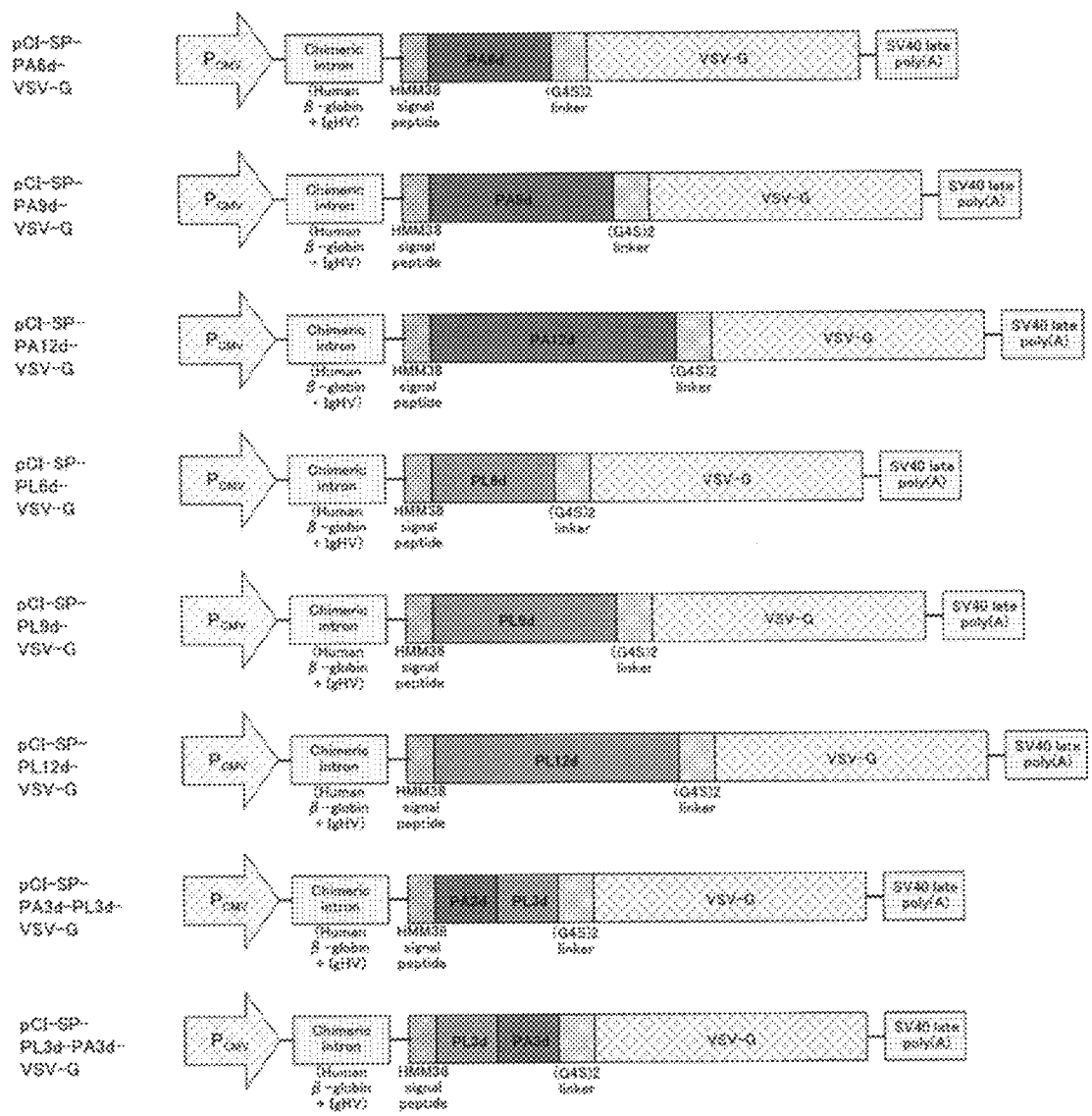

[Fig. 3]
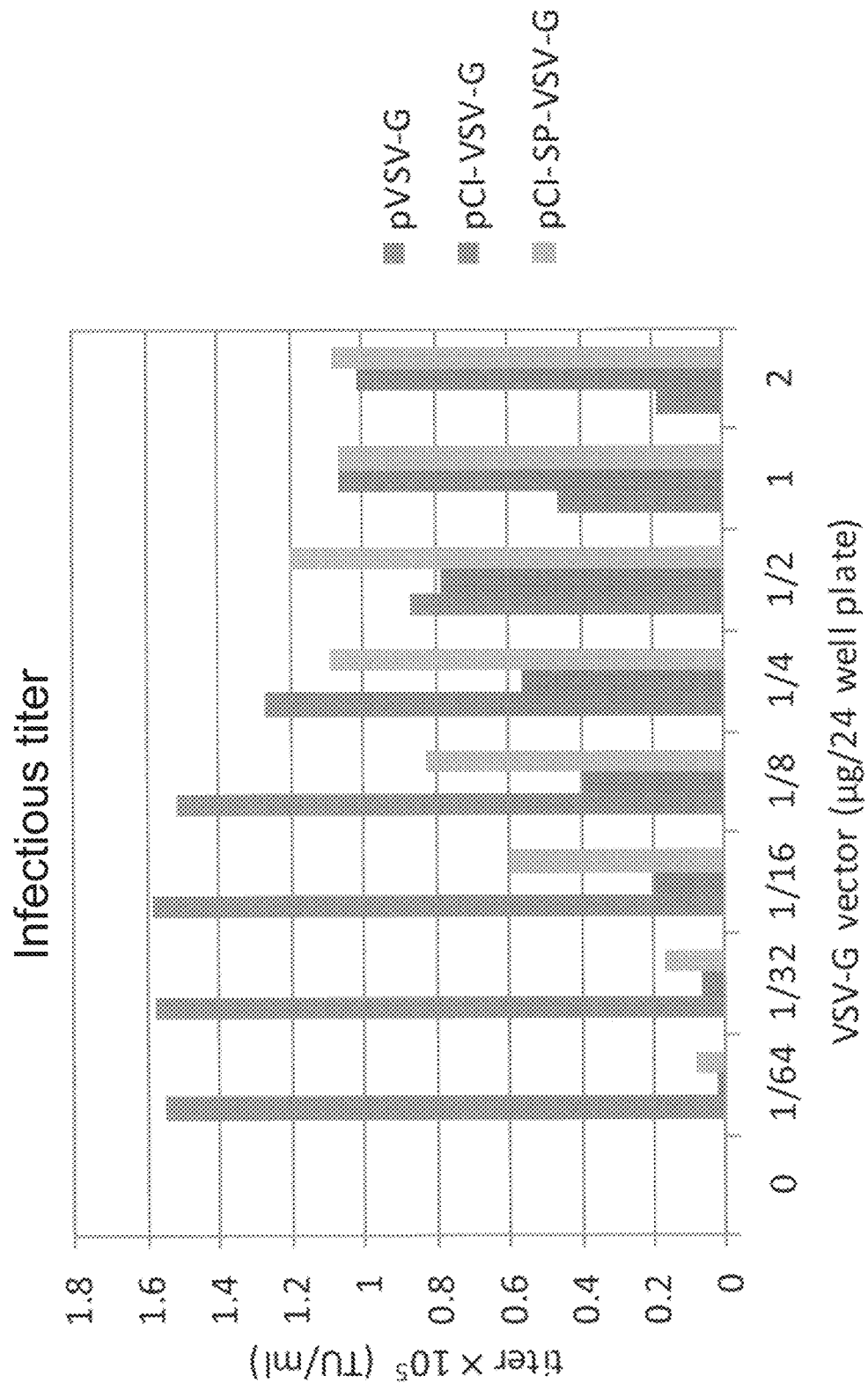

[Fig. 4]
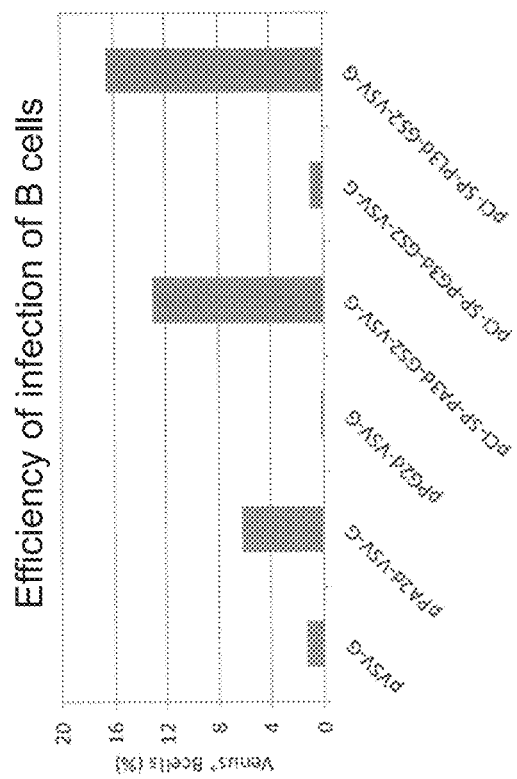
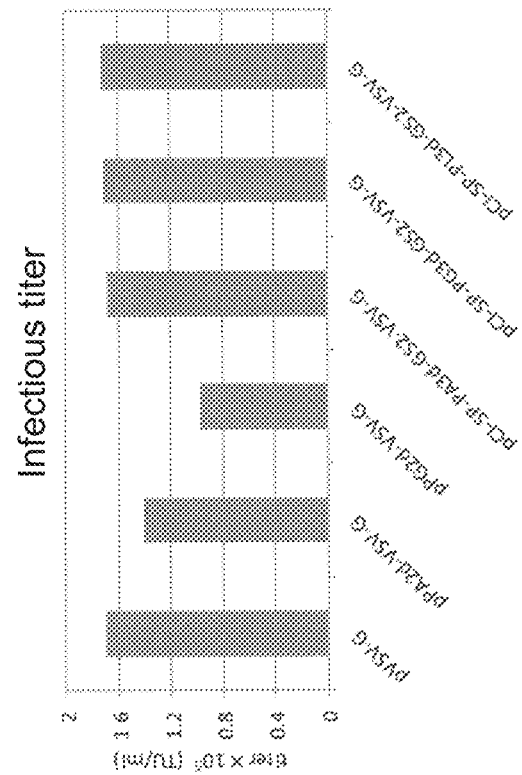

[Fig. 5]
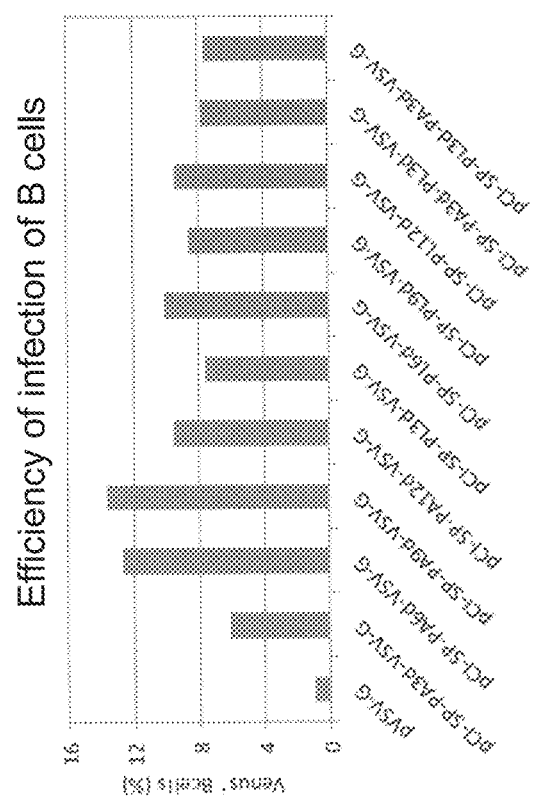

[Fig. 6]
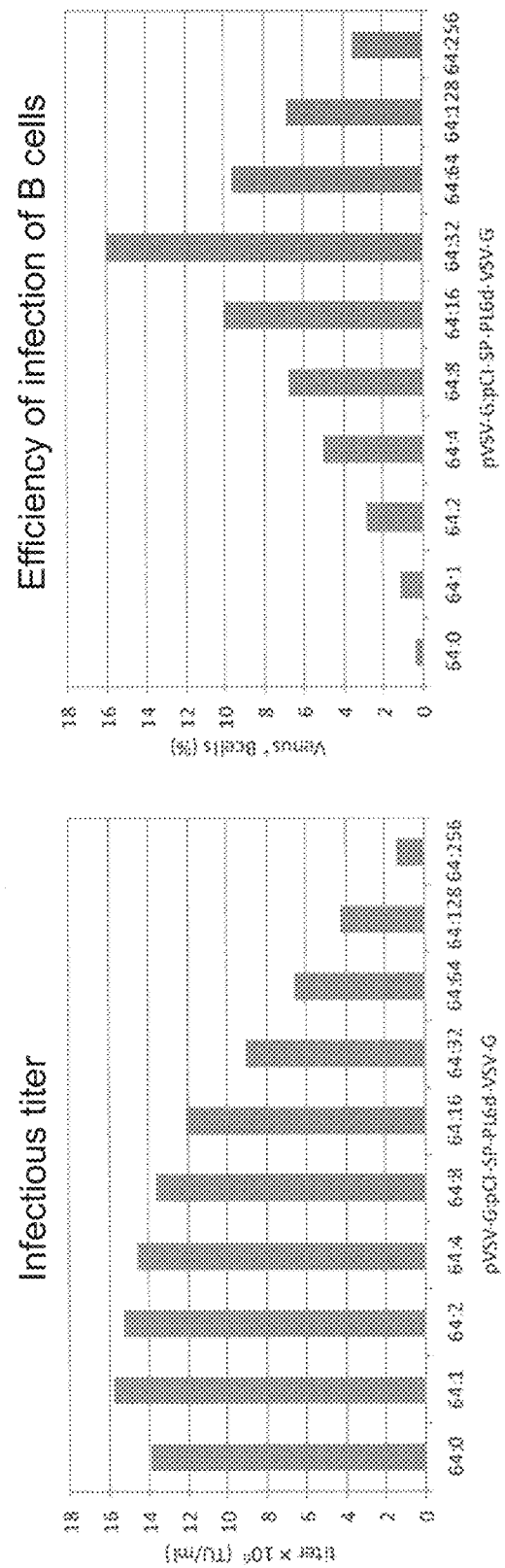

[Fig. 7]
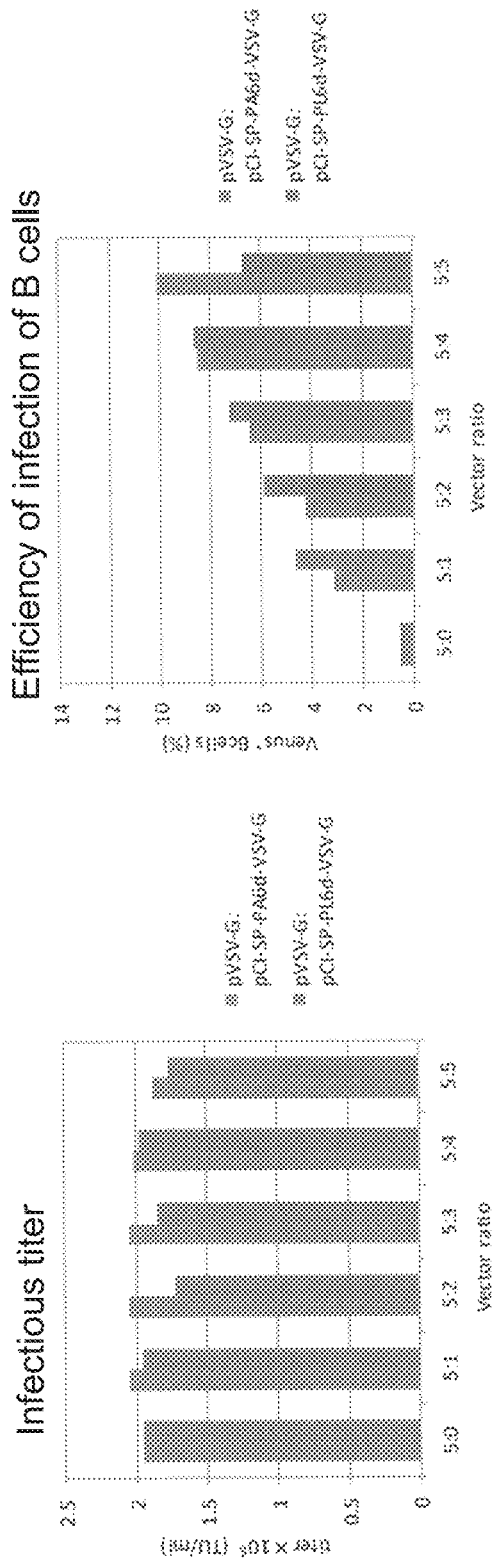

[Fig. 8]
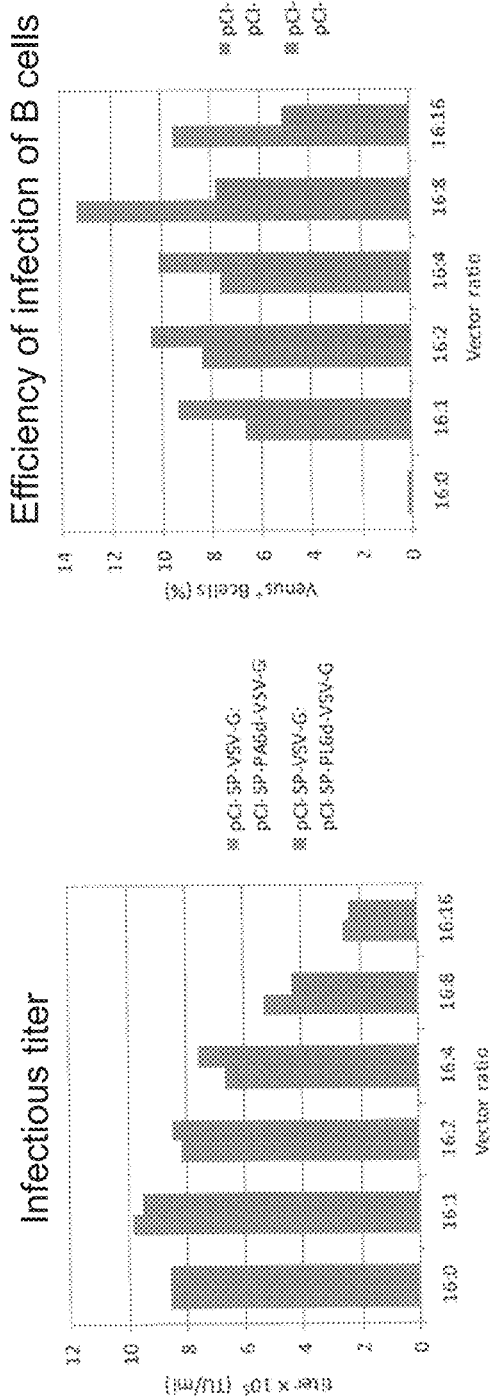

[Fig. 9]
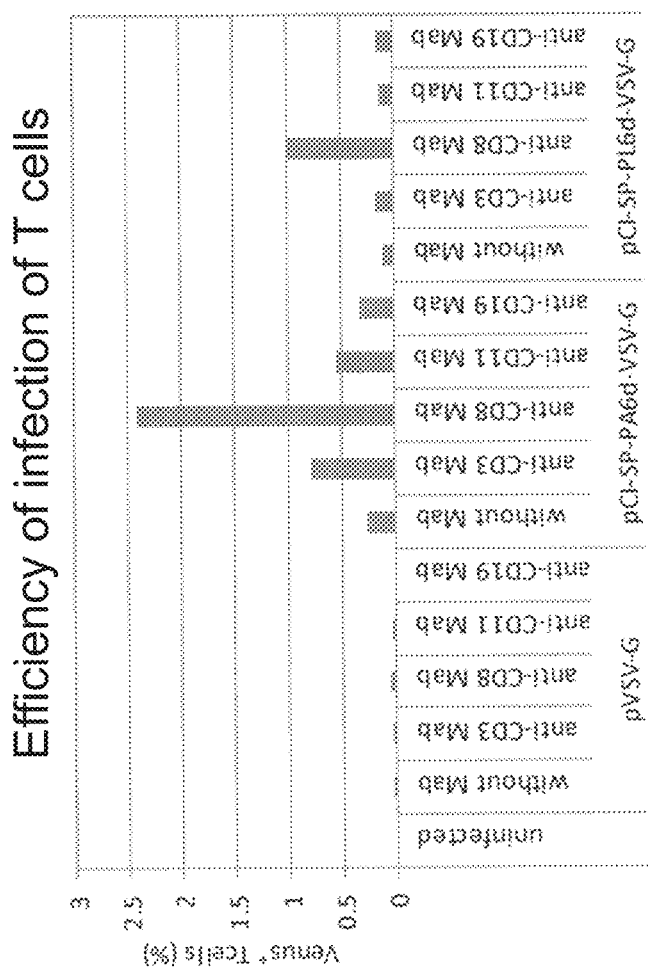
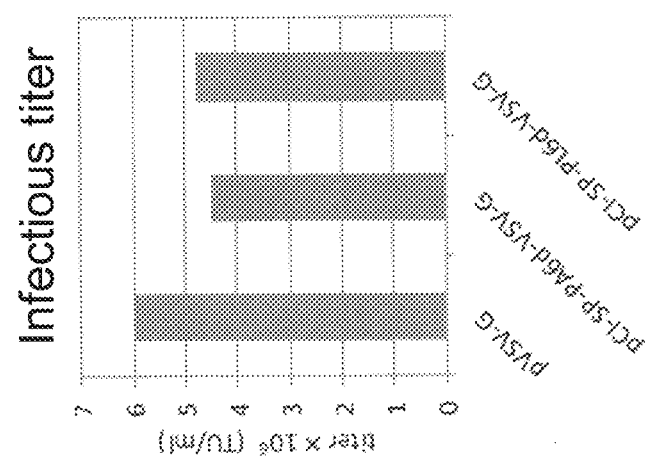

[Fig. 10]
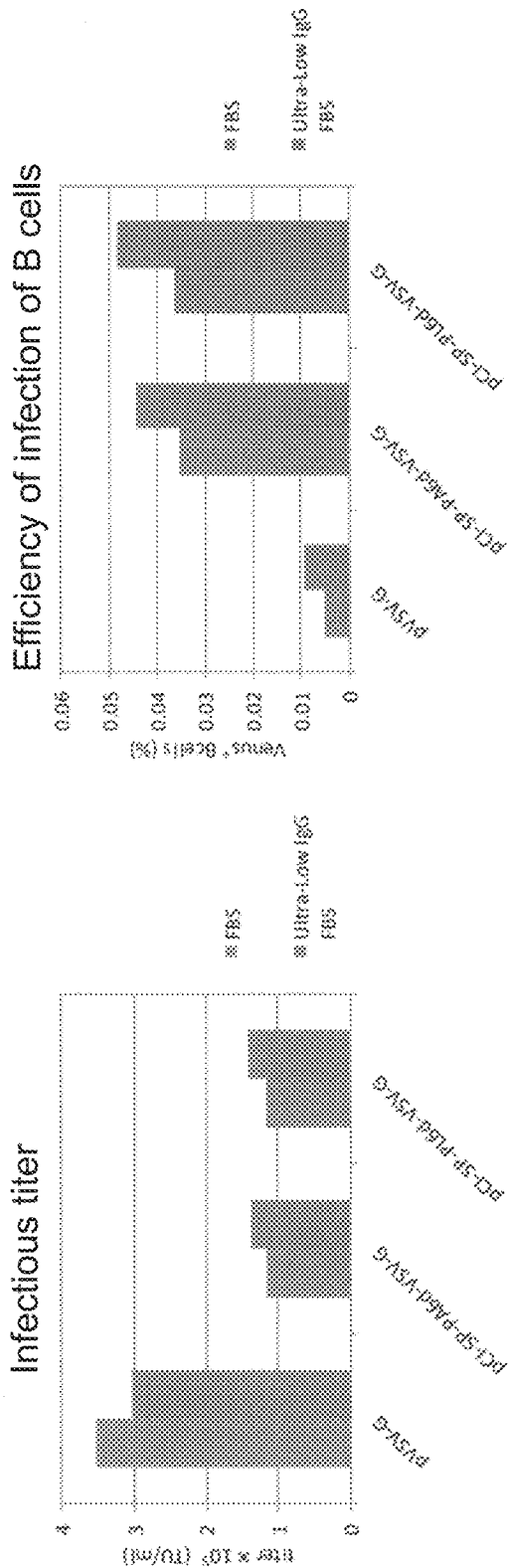

[Fig. 11]

Efficiency of infection of B cells

Infectious titer

[Fig. 12]
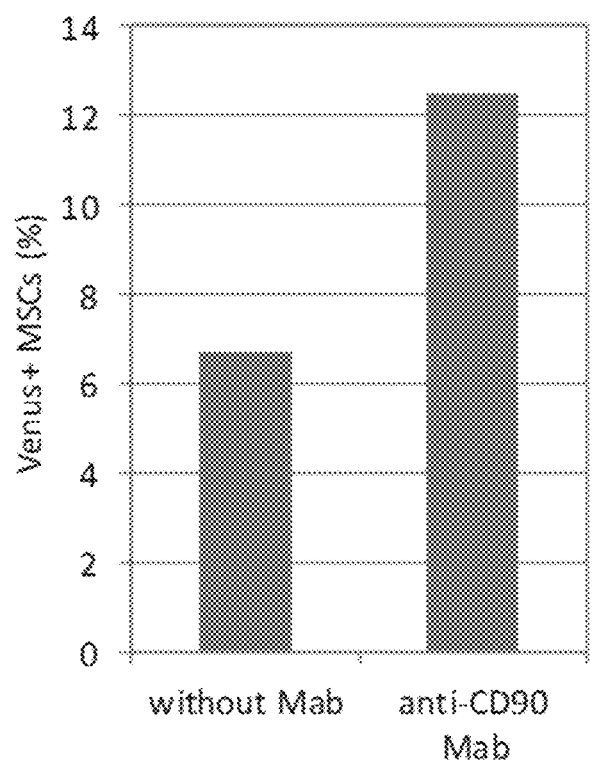

SEQUENCE LISTING

<160> NUMBER OF SEQ ID NOS: 24

<210> SEQ ID NO 1
<211> LENGTH: 553
<212> TYPE: DNA
<213> ORGANISM: Staphylococcus aureus

<400> SEQUENCE: 1

```
ctcgaggaat tctgacacta tgagaagcct gctgatcctg gtgctgtgct tcctgcccct        60
ggccgctctg ggcgacaaca agttcaataa ggagcagcag aacgccttct acgagatcct       120
gcacctgccc aacctgaatg aggaacagag aaacgccttc atccagagcc tgaaggacga       180
tccctcccag agcgccaacc tgctggctga ggccaagaaa ctgaacgacg cccaggctcc       240
caaagtggac aataagttca acaaagaaca gcagaatgct ttttatgaaa ttctgcatct       300
gcctaatctg aacgaagagc agcggaatgc tttttattcag tccctgaaag atgaccctag       360
ccagtccgct aatctgctgg ccgaagctaa aaagctgaat gatgctcagg cccctaaagt       420
ggagttcggg ggcggaggca gcggagggggg cggatcatgc aagttcacca tcgtgtttcc       480
ccacaaccag aagggcaact ggaagaatgt gcccagcaac taccactact gccccagctc       540
ctctgattta aat                                                         553
```

<210> SEQ ID NO 2
<211> LENGTH: 571
<212> TYPE: DNA
<213> ORGANISM: group G streptococcus

<400> SEQUENCE: 2

```
ctcgaggaat tctgacacta tgagggcatg gatcttcttc ctcctttgtc tggcagggag      60
agctttggcc acctacaagc tgattctgaa cggcaagacc ctgaaaggag agacaaccac     120
tgaagccgta gatgctgcta cagcagagaa ggtgttcaaa cagtatgcca acgacaatgg     180
cgttgatggg gaatggacgt atgacgacgc cactaagacc tttactgtga ccgagaaacc     240
tgaggtcata gacgccagtg agctgacacc agccgtaaca acctacaaac tcgtgattaa     300
tggcaagaca ctgaagggcg aaactaccac taaagctgtg gatgctgaaa ccgcagagaa     360
ggcctttaag caatacgcga atgacaatgg ggttgatggt gtgtggacct atgacgatgc     420
gacaaagacg tttacggtca cagaaggagg tggagggtct ggcggtggcg gatcctgcaa     480
attcactatc gtgtttccgc ataaccagaa aggaaactgg aagaatgtcc ccagcaacta     540
ccactattgc ccctcaagct ccgatttaaa t                                    571
```

<210> SEQ ID NO 3
<211> LENGTH: 194
<212> TYPE: DNA
<213> ORGANISM: Artificial Sequence
<220> FEATURE:
<223> OTHER INFORMATION: signal peptide

<400> SEQUENCE: 3

```
ctcgagctgc agcggccgcg gaacacagag aaaccgccat gtggtggaga ctgtggtggc      60
tgctgctgct gctgctgctg ctgtggccta tggtgtgggc caagttcacc atcgtgtttc     120
cccacaacca gaagggcaac tggaagaatg tgcccagcaa ctaccactac tgccccagct     180
cctctgattt aaat                                                       194
```

<210> SEQ ID NO 4
<211> LENGTH: 224
<212> TYPE: DNA
<213> ORGANISM: Artificial Sequence
<220> FEATURE:
<223> OTHER INFORMATION: signal peptide, linker

<400> SEQUENCE: 4

```
ctcgagctgc agcggccgcg gaacacagag aaaccgccat gtggtggaga ctgtggtggc      60
tgctgctgct gctgctgctg ctgtggccta tggtgtgggc cggcggggga ggcagcggag     120
ggggcggatc aaagttcacc atcgtgtttc cccacaacca gaagggcaac tggaagaatg     180
tgcccagcaa ctaccactac tgccccagct cctctgattt aaat                      224
```

<210> SEQ ID NO 5
<211> LENGTH: 516
<212> TYPE: DNA
<213> ORGANISM: Staphylococcus aureus

<400> SEQUENCE: 5

```
ggcgccgaca acaacttcaa taaggagcaa cagaatgcgt tttacgagat tctgaacatg      60
cccaatctga atgaggaaca gaggaatgga ttcattcaga gcctgaagga cgatccttct     120
cagtcagcca atctgctgtc tgaggccaag aaactgaacg aatcccaagc accaaaagcc     180
gacaataagt tcaacaagga acagcagaac gccttttacg agatccttca cttgcccaac     240
```

```
ctgaatgaag agcagagaaa cgggtttatc cagtcactca aagacgaccc aagtcagagc    300
gctaatctgt tggcagaggc taagaagctg aacgatgctc aagcaccgaa agccgataac    360
aagttcaaca aagagcagca aaacgcgttc tatgagattc ttcatctgcc taacctcacc    420
gaagaacagc ggaatggctt tatccagagc ctcaaagacg atcccagtgt gtccaaggag    480
atacttgctg aagccaagaa actcaatgat gccggc                              516
```

<210> SEQ ID NO 6
<211> LENGTH: 591
<212> TYPE: DNA
<213> ORGANISM: group G streptococcus

<400> SEQUENCE: 6

```
agtacttaca aactgatcct gaatgggaaa accctgaagg gtgagactac cacagaagct     60
gtggatgctg ccactgctga aaggtgttc aagcaatacg ccaacgacaa tggggtcgat    120
ggagagtgga cctatgacga tgcgacaaag acgtttacag tgactgagaa acccgaagtg    180
atagacgctt ccgagttgac ccctgccgtg accacgtaca agctggtgat caatggcaag    240
acactcaagg gagaaaccac tactgaagct gtcgacgcag ctacagcgga gaaggtcttt    300
aagcagtacg caaacgacaa cggtgtagat ggcgagtgga cttatgacga cgcaaccaaa    360
accttcacag ttaccgagaa accagaagtc attgacgcaa gcgagcttac accggcagtg    420
accacctaca aactggtgat taacgggaaa accctcaaag agagactac aactaaggcc      480
gttgatgccg aaacagccga aaaggccttc aaacagtatg ccaacgataa tggcgttgat    540
ggcgtatgga cctatgatga cgccacaaag acttttacgg tgacggagct c              591
```

<210> SEQ ID NO 7
<211> LENGTH: 634
<212> TYPE: DNA
<213> ORGANISM: Peptostreptococcus magnus

<400> SEQUENCE: 7

```
gagtcccggg gaagtgacga taaaggcgaa tctgatcttc gctgacggaa gcactcagaa     60
tgccgagttt aagggtacct tcgcaaaagc tgtgtccgac gcttatgcct atgccgatgc    120
tctgaagaaa gacaatggcg aatacacagt tgacgtagcc gataagggac ttacactgaa    180
catcaagttt gccggtaaga aggagaaacc agaggaaccc aaggaagagg tgaccattaa    240
ggtcaacctg attttcgccg atggcaaaac acagactgca gagttcaaag gacctttga    300
ggaggcaact gcaaaagcct acgcttatgc agacttgctg gccaaagaga atggcgagta    360
taccgccgat ctggaggacg gaggcaacac cattaacatc aagttcgctg ggaaagaaac    420
accgaaaacc cctgaagaac cgaaagaaga agtcacgatc aaggtgaacc tcatatttgc    480
cgacggtaag atccaaacag cggagtttaa gggcactttc gaggaagcaa ctgccaaagc    540
gtacgcttac gcaaacctct tggctaaaga gaatggggag tacacagccg atcttgagga    600
tggagggaat accatcaaca ttaagtttgc cggc                                634
```

<210> SEQ ID NO 8
<211> LENGTH: 50
<212> TYPE: DNA
<213> ORGANISM: Artificial Sequence
<220> FEATURE:
<223> OTHER INFORMATION: primer

<400> SEQUENCE: 8
acggtcgacg ctagcccaca accatggtga gcaagggcga ggagctgttc            50

<210> SEQ ID NO 9
<211> LENGTH: 70
<212> TYPE: DNA
<213> ORGANISM: Artificial Sequence
<220> FEATURE:
<223> OTHER INFORMATION: primer

<400> SEQUENCE: 9
gataagcttg atccctcgat gttaactcta gaggatccgc ggccgctgca gaattcttac      60
ttgtacagct                                                            70

<210> SEQ ID NO 10
<211> LENGTH: 54
<212> TYPE: DNA
<213> ORGANISM: Artificial Sequence
<220> FEATURE:
<223> OTHER INFORMATION: linker

<400> SEQUENCE: 10
ggccgctcga gcacgtgtac gtagaattca agcttcgcga gtcgacgtat acat           54

<210> SEQ ID NO 11
<211> LENGTH: 52
<212> TYPE: DNA
<213> ORGANISM: Artificial Sequence
<220> FEATURE:
<223> OTHER INFORMATION: linker

<400> SEQUENCE: 11
cgatgtatac gtcgactcgc gaagcttgaa ttctacgtac acgtgctcga gc             52

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
tttcgggttt attacaggga cagc                                            24

<210> SEQ ID NO 13
<211> LENGTH: 35
<212> TYPE: DNA
<213> ORGANISM: Artificial Sequence
<220> FEATURE:
<223> OTHER INFORMATION: primer

<400> SEQUENCE: 13
gttgtatgtt tcgatcatgg ttgtggccat attat                                35

<210> SEQ ID NO 14
<211> LENGTH: 35
<212> TYPE: DNA
<213> ORGANISM: Artificial Sequence
<220> FEATURE:
<223> OTHER INFORMATION: primer

<400> SEQUENCE: 14
ataatatggc cacaaccatg atcgaaacat acaac                                35

<210> SEQ ID NO 15
<211> LENGTH: 54

<212> TYPE: DNA
<213> ORGANISM: Artificial Sequence
<220> FEATURE:
<223> OTHER INFORMATION: primer

<400> SEQUENCE: 15
tcgaagcatt aaccctcact aagaattccc tcagagtttg agtaagccaa agga        54

<210> SEQ ID NO 16
<211> LENGTH: 60
<212> TYPE: DNA
<213> ORGANISM: Artificial Sequence
<220> FEATURE:
<223> OTHER INFORMATION: primer

<400> SEQUENCE: 16
cttcgcggcc gcggaacaca gagaaaccgc catggatgac tccacagaaa gggagcagtc        60

<210> SEQ ID NO 17
<211> LENGTH: 60
<212> TYPE: DNA
<213> ORGANISM: Artificial Sequence
<220> FEATURE:
<223> OTHER INFORMATION: primer

<400> SEQUENCE: 17
tctggcggcc gcattaaccc tcactaagaa ttgcctcaca gcagtttcaa tgcaccaaaa        60

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
atgaccgagt acaagcccac ggtg        24

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
ctaggcaccg ggcttgcggg tcat        24

<210> SEQ ID NO 20
<211> LENGTH: 27
<212> TYPE: DNA
<213> ORGANISM: Artificial Sequence
<220> FEATURE:
<223> OTHER INFORMATION: linker

<400> SEQUENCE: 20
tcgagtcgcg aattctagat atcgata        27

<210> SEQ ID NO 21
<211> LENGTH: 27
<212> TYPE: DNA
<213> ORGANISM: Artificial Sequence
<220> FEATURE:
<223> OTHER INFORMATION: linker

<400> SEQUENCE: 21
cgcgtatcga tatctagaat tcgcgac                                              27

<210> SEQ ID NO 22
<211> LENGTH: 886
<212> TYPE: DNA
<213> ORGANISM: Homo sapiens

<400> SEQUENCE: 22
gctagcaccg ccatgagagc ctggatcttc tttctgctct gcctggccgg aagagccctg    60
gctgcctcct ggagccaccc ccagttcgag aagggcgccg aggtggaggc cctggagaag   120
aaagtggccg ctctggagag caaggtgcag gccctggaga gaaagtggag ggccctggag   180
cacggaggcg ccggaggcgg aggctccggc ggaggaggct ctggaggcgg gggcagcgac   240
aagatagaag atgaaaggaa tcttcatgaa gattttgtat tcatgaaaac gatacagaga   300
tgcaacacag agaaagatc cttatcctta ctgaactgtg aggagattaa agccagttt    360
gaaggctttg tgaaggatat aatgttaaac aaagaggaga cgaagaaaga aaacagcttt   420
gaaatgcaaa aaggtgatca gaatcctcaa attgcggcac atgtcataag tgaggccagc   480
agtaaaacaa catctgtgtt acagtgggct gaaaaaggat actacaccat gagcaacaac   540
ttggtaaccc tggaaaatgg gaaacagctg accgttaaaa gacaaggact ctattatatc   600
tatgcccaag tcaccttctg ttccaatcgg gaagcttcga gtcaagctcc atttatagcc   660
agcctctgcc taaagtcccc cggtagattc gagagaatct tactcagagc tgcaaatacc   720
cacagttccg ccaaaccttg cgggcaacaa tccattcact tgggaggagt atttgaattg   780
caaccaggtg cttcggtgtt tgtcaatgtg actgatccaa gccaagtgag ccatggcact   840
ggcttcacgt cctttggctt actcaaactc tgagctgccg gaattc                 886

<210> SEQ ID NO 23
<211> LENGTH: 907
<212> TYPE: DNA
<213> ORGANISM: Homo sapiens

<400> SEQUENCE: 23
gctagcaccg ccatgagagc ctggatcttc tttctgctct gcctggccgg aagagccctg    60
gctgcctcct ggagccaccc ccagttcgag aagggcgccg aggtggaggc cctggagaag   120
aaagtggccg ctctggagag caaggtgcag gccctggaga gaaagtggag ggccctggag   180
cacggaggcg ccggaggcgg aggctccggc ggaggaggct ctggaggcgg gggcagccag   240
gtggccgccc tgcaagggga cctggccagc ctccgggcag agctgcaggg ccaccacgcg   300
gagaagctgc agcaggagc aggagccccc aaggccggcc tggaggaagc tccagctgtc   360
accgcgggac tgaaaatctt tgaaccacca gctccaggag aaggcaactc cagtcagaac   420
agcagaaata gcgtgccgt tcagggtcca gaagaaacag tcactcaaga ctgcttgcaa   480
ctgattgcag acagtgaaac accaactata caaaaggat cttacacatt tgttccatgg   540
cttctcagct ttaaaagggg aagtgcccta gaagaaaaag agaataaaat attggtcaaa   600
gaaactggtt acttttttat atatggtcag gttttatata ctgataagac ctacgccatg   660
ggacatctaa ttcagaggaa gaaggtccat gtctttgggg atgaattgag tctggtgact   720
ttgtttcgat gtattcaaaa tatgcctgaa acactaccca ataattcctg ctattcagct   780
ggcattgcaa aactggaaga aggagatgaa ctccaacttg caataccaag agaaaatgca   840
caaatatcac tggatggaga tgtcacattt tttggtgcat tgaaactgct gtgagctgcc   900
ggaattc                                                            907

-continued

```
<210> SEQ ID NO 24
<211> LENGTH: 29
<212> TYPE: PRT
<213> ORGANISM: Artificial Sequence
<220> FEATURE:
<223> OTHER INFORMATION: coiled coil

<400> SEQUENCE: 24

Glu Val Glu Ala Leu Glu Lys Lys Val Ala Ala Leu Glu Ser Lys Val
1               5                   10                  15

Gln Ala Leu Glu Lys Lys Val Glu Ala Leu Glu His Gly
            20                  25
```

METHOD FOR PRODUCING TRANSGENIC CELL

TECHNICAL FIELD

The present invention relates to a method for producing a transgenic cell, comprising transferring a foreign gene into a target cell by using a virus comprising a chimeric envelope protein. More specifically, the present invention relates to a method for producing a transgenic cell, comprising performing gene transfer by using a virus comprising a chimeric protein of an antibody-binding protein and a vesicular stomatitis virus G (VSV-G) protein.

BACKGROUND ART

A wide variety of virus-derived vectors have been used for the purpose of transferring and expressing a desired gene in eukaryotic cells. A desired gene operably linked to a promoter that operates in a target cell can be inserted in a viral gene to prepare a viral vector. A target cell can be infected with the viral vector to express the desired gene in place of the viral gene. Since the entire viral gene is not present in the viral vector, even if a target cell is infected with the viral vector, viral particles are not produced. Examples of the virus for use in the infection of a target cell of a mammal such as human include herpes virus, adenovirus, adeno-associated virus and retrovirus.

Patent Document 1 describes a viral vector for transducing a target cell which comprises a gene encoding a chimeric envelope protein containing a portion of an IgG-binding domain of protein A wherein the envelope protein comprises a portion of a gp70 protein of a murine leukemia virus or an avian leukemia virus, and the envelope protein is operable to direct the assembly of fragments into a viral particle.

Non Patent Document 1 discloses that a gene sequence expressing Z domain of Protein A is inserted into a plasmid expressing VSV-G in the envelop to produce a plasmid expressing a fusion protein of Protein-A Z domain and VSV-G, and the plasmid is transferred into a viral vector producing cell, i.e., 293FT cell, to produce a lentiviral vector expressing a desired envelop protein; and that, thereafter, the lentiviral vector is added to a plate coated with a human IgG antibody and the plate was washed, and then, an adherent cell was seeded to the plate to infect the cell with the viral vector. To describe more specifically, the document discloses that an antibody is immobilized to a plate surface and a lentiviral vector is concentrated on the plate surface by use of the interaction between the antibody and Z domain, and the cells are then infected with the viral vector by taking advantage of an adherent cell, which adheres to the plate surface.

PRIOR ART DOCUMENTS

Patent Document

Patent Document 1: JP Patent Publication (Kohyo) No. 2002-516570 A

Non-Patent Document

Non-Patent Document 1: Y. Kameyama et al., Journal of Virological Methods 153 (2008) 49-54

SUMMARY OF INVENTION

Object to be Solved by the Invention

In the method of Patent Document 1, a retrovirus having a chimeric protein comprising gp70 protein of a mouse leukemia virus or an avian leukemia virus is used; however, the method has a problem in that the types of target cells are limited. In the method of Non Patent Document 1, a gene transfer is performed by seeding an adhesive target cell onto a plate having a virus immobilized thereon. In short, the target cell is infected with a virus not through an antibody. Accordingly, it is difficult to apply the method of Non Patent Document 1 to cells (for example, floating cells) except adherent cells. In addition, since "antibody targeting" is not used in viral infection, it is also difficult to transfer a gene into human primary cells to which a gene is not easily transferred.

An object to be solved by the present invention is to provide a method for producing a transgenic cell, which enables to efficiently transfer a gene into a wide variety of cells regardless of cell types, in particular, even in a human primary cell. Another object to be solved by the present invention is to provide a virus comprising a chimeric protein of an antibody-binding protein and a vesicular stomatitis virus G (VSV-G) protein for use in the method for producing a transgenic cell, and a gene therapeutic agent comprising the virus. Another object to be solved by the present invention is to provide a transgenic cell obtained by the method for producing a transgenic cell.

Means for Solving the Objects

The present inventors conducted intensive studies with a view to attaining the aforementioned objects. As a result, they have found that a virus comprising a chimeric protein of an antibody-binding protein and a vesicular stomatitis virus G (VSV-G) protein, can be contacted with a target cell and an antibody specific to the target cell, and/or a target cell comprising a membrane antibody to highly efficiently infect the target cell with the virus, thereby allowing to transfer the gene into the target cell.

According to the present invention, the following are provided:
(1) A method for producing a transgenic cell, comprising contacting, in vitro,
   (i) a virus comprising: a chimeric protein of an antibody-binding protein and a vesicular stomatitis virus G (VSV-G) protein; and a foreign gene, with
   (ii) a target cell and an antibody specific to the target cell, and/or a target cell comprising a membrane antibody, to infect the target cell with the virus.
(2) The method for producing a transgenic cell according to (1), wherein the antibody-binding protein comprises either one or both of an IgG-binding domain of protein A and an IgG-binding domain of protein L.
(3) The method for producing a transgenic cell according to (2), wherein the antibody-binding protein comprises 3 or more IgG-binding domains of protein A.
(4) The method for producing a transgenic cell according to (2) or (3), wherein the antibody-binding protein comprises 3 or more IgG-binding domains of protein L.
(5) The method for producing a transgenic cell according to any one of (1) to (4), wherein, in the chimeric protein, the antibody-binding protein is present at the N-terminal side of the vesicular stomatitis virus G (VSV-G) protein.

(6) The method for producing a transgenic cell according to any one of (1) to (5), wherein the virus is a retrovirus.
(7) The method for producing a transgenic cell according to (6), wherein the retrovirus is a lentivirus.
(8) The method for producing a transgenic cell according to any one of (1) to (7), wherein the target cell is at least one of a human primary cell, a human induced pluripotent stem cell (iPS cell), a human embryonic stem cell (ES cell), a human mesenchymal stem cell, and cells differentiated and induced from said cells.
(9) The method for producing a transgenic cell according to any one of (1) to (8), wherein the target cell is a peripheral blood mononuclear cell.
(10) The method for producing a transgenic cell according to any one of (1) to (8), wherein the target cell is human B cell, human T cell or a human mesenchymal stem cell.
(11) The method for producing a transgenic cell according to any one of (1) to (10), wherein the target cell is human T cell; and the antibody specific to the target cell is at least one selected from an anti-human CD3 antibody, an anti-human CD8a antibody and an anti-human CD11a antibody.
(12) The method for producing a transgenic cell according to any one of (1) to (10), wherein the target cell is human B cell; and the virus is contacted with the target cell in vitro in the presence of at least one stimulus selected from a stimulus via IL-4, ODN 2006 and CD40 receptors and a stimulus via a BAFF receptor.
(13) The method for producing a transgenic cell according to any one of (1) to (10), wherein the target cell is a human mesenchymal stem cell; and the antibody specific to the target cell is an anti-human CD90 antibody.
(14) The method for producing a transgenic cell according to any one of (1) to (11), wherein a virus comprising a chimeric protein of an antibody-binding protein and a vesicular stomatitis virus G (VSV-G) protein comprises vesicular stomatitis virus G (VSV-G) protein in addition to the chimeric protein.
(15) The method for producing a transgenic cell according to (14), wherein a molar ratio of the chimeric protein and the vesicular stomatitis virus G (VSV-G) protein in the virus falls within a range of 1:1 to 1:512.
(16) The method for producing a transgenic cell according to any one of (1) to (15), wherein the virus comprising a chimeric protein of an antibody-binding protein and a vesicular stomatitis virus G (VSV-G) protein is produced by using a plasmid vector which contains a nucleotide sequence encoding the chimeric protein of an antibody-binding protein and a vesicular stomatitis virus G (VSV-G) protein, in combination with a plasmid vector which does not comprise a nucleotide sequence encoding the antibody-binding protein and comprises a nucleotide sequence encoding the vesicular stomatitis virus G (VSV-G) protein.
(17) The method for producing a transgenic cell according to (16), wherein a mass ratio of the plasmid vector which does not comprise a nucleotide sequence encoding the antibody-binding protein and comprises a nucleotide sequence encoding the vesicular stomatitis virus G (VSV-G) protein, and a plasmid vector which comprises a nucleotide sequence encoding the chimeric protein of an antibody-binding protein and a vesicular stomatitis virus G (VSV-G) protein falls within a range of 64:1 to 64:256.
(18) A virus comprising: a chimeric protein of an antibody-binding protein and a vesicular stomatitis virus G (VSV-G) protein; and a foreign gene, wherein the antibody-binding protein comprises an IgG-binding domain of protein L and/or comprises 3 or more IgG-binding domains of protein A.
(19) The virus according to (18), wherein the virus is a retrovirus.
(20) The virus according to (19), wherein the retrovirus is a lentivirus.
(21) A gene therapeutic agent comprising the virus according to any one of (18) to (20).
(22) A transgenic cell obtained by the method for producing a transgenic cell according to any one of (1) to (17).
(23) A transgenic cell infected with the virus according to any one of (18) to (20).
(24) A plasmid vector comprising a nucleotide sequence encoding a chimeric protein of an antibody-binding protein and a vesicular stomatitis virus G (VSV-G) protein.
(25) A kit for carrying out a method for producing a transgenic cell according to any one of (1) to (17), comprising: a target cell selected from a human primary cell, a human induced pluripotent stem cell (iPS cell), a human embryonic stem cell (ES cell) or a human mesenchymal stem cell; and an antibody specific to the target cell.

Advantageous Effects of Invention

According to the method for producing a transgenic cell of the present invention, a gene can be efficiently transferred into a target cell.

BRIEF DESCRIPTION OF DRAWINGS

FIG. 1 shows a schematic diagram of chimeric envelope protein expression vectors according to Example 1 of the present invention.
FIG. 2 shows a schematic diagram of chimeric envelope protein expression vectors according to Example 1 of the present invention.
FIG. 3 is a graph showing the relationship between the concentration of VSV-G vector and titer in Example 6 of the present invention. In each group of bar charts, the left bar represents pVSV-G; the middle bar represents pCI-VSV-G; and the right bar represents pCI-SP-VSV-G.
FIG. 4 is a graph showing evaluation results of the expression vector for the chimeric envelope protein in Example 7 of the present invention.
FIG. 5 is a graph showing evaluation results of the number of domains of the antibody-binding protein and efficiency of infection in Example 8 of the present invention.
FIG. 6 is a graph showing evaluation results of the ratio of pVSV-G and pCI-SP-PL6d-VSV-G in Example 9 of the present invention.
FIG. 7 is a graph showing evaluation results of the ratio of pVSV-G and expression vector for the chimeric envelope protein in Example 9 of the present invention. In each group of bar charts, the left bar represents the ratio of pVSV-G: pCI-SP-PA6d-VSV-G and the right bar represents the ratio of pVSV-G:pCI-SP-PL6d-VSV-G.
FIG. 8 is a graph showing evaluation results of the ratio of pCI-SP-VSV-G and chimeric envelope protein expression vector in Example 9 of the present invention. In each group of bar charts, the left bar represents the ratio of pCI-SP-VSV-G:pCI-SP-PA6d-VSV-G and the right bar represents the ratio of pCI-SP-VSV-GpCI-SP-PL6d-VSV-G.
FIG. 9 is a graph showing the evaluation results of infection to T cells via the antibody in Example 10 of the present invention.
FIG. 10 is a graph showing the evaluation results of infection to B cells with a retrovirus having a chimeric envelope protein in Example 11 of the present invention. In each group of bar charts, the left graph bar represents FBS and the right bar represents Ultra-Low IgGFBS.

FIG. 11 is a graph showing the evaluation results of infection of a concentrated lentivirus to B cell in Example 12 of the present invention.

FIG. 12 is a graph showing the evaluation results of infection of a concentrated lentivirus to MSC in Example 13 of the present invention.

EMBODIMENTS OF CARRYING OUT THE INVENTION

Embodiments of the present invention will be described below.

The method for producing a transgenic cell according to the present invention is a method for producing a transgenic cell, comprising contacting, in vitro, (i) a virus comprising a chimeric protein of an antibody-binding protein and a vesicular stomatitis virus G (VSV-G) protein; and a foreign gene, with (ii) a target cell and an antibody specific to the target cell, and/or a target cell comprising a membrane antibody, to infect the target cell with the virus.

(1) Virus comprising: a chimeric protein of an antibody-binding protein and a vesicular stomatitis virus G (VSV-G) protein; and a foreign gene The virus to be used in the present invention comprises a chimeric protein of an antibody-binding protein and a vesicular stomatitis virus G (VSV-G) protein.

Examples of the virus to be used in the present invention includes, but are not particularly limited to, a retrovirus, a baculovirus, a Japanese encephalitis virus and C hepatitis virus.

As the retrovirus, e.g., a lentiviral vector derived from Human immunodeficiency virus (HIV), Simian Immunodeficiency Virus (SIV) or Bovine immunodeficiency virus (BIV); or a retroviral vector derived from a murine leukemia virus (MoMLV) or a mouse stem cell virus (MSCV) can be used. Particularly, a replication-incompetent retroviral vector is suitably used.

The virus to be used in the present invention comprises a chimeric protein of an antibody-binding protein and a vesicular stomatitis virus G (VSV-G) protein.

The vesicular stomatitis virus G (VSV-G) protein is an envelope protein. A VSV-G receptor, which is a membrane component, i.e., phospholipid, is widely present in membrane of animal cells. Because of this, according to the method of the present invention, a desired foreign gene can be transferred into various animal cells.

In the present invention, the antibody-binding protein preferably comprises either one or both of an IgG-binding domain of protein A and an IgG-binding domain of protein L.

Protein A is a cell-wall protein produced by a gram-positive bacterium, *Staphylococcus aureus* and constituted of a signal sequence S, 5 immunoglobulin (IgG) binding domains (E domain, D domain, A domain, B domain, C domain) and a cell-wall binding domain, i.e., XM region (JP Patent No. 5952185). The IgG-binding domain of protein A according to the present invention may be a mutant as long as it can bind to IgG.

As Protein L, those derived from two strains of *Finegoldia magna* are known. One is protein L derived from 3316 strain and the other is protein L derived from 312 strain. Protein L derived from 3316 strain has 4 IgG-binding domains; whereas protein L derived from 312 strain has 5 IgG-binding domains (JP Patent Publication (Kokai) No. 2016-79149, FIG. 1). The IgG-binding domain of protein L according to the present invention may be a mutant as long as it can binds to IgG.

Preferably, the antibody-binding protein can comprise 3 or more IgG-binding domains of protein A; for example, the number of domains may be 3 to 15, 3 to 12, 3 to 9 or 3 to 6.

Preferably, the antibody-binding protein can comprise 3 or more IgG-binding domains of protein L; for example, the number of domains may be 3 to 15, 3 to 12, 3 to 9 or 3 to 6.

If the antibody-binding protein comprises both IgG-binding domains of protein A and IgG-binding domains of protein L, the total number of domains is preferably 3 or more; for example, may be 3 to 15, 3 to 12, 3 to 9 or 3 to 6.

An example of the virus to be used in the present invention is a virus comprising: a chimeric protein of an antibody-binding protein and a vesicular stomatitis virus G (VSV-G) protein; and a foreign gene, in which the antibody-binding protein comprises IgG-binding domains of protein L and/or 3 or more IgG-binding domains of protein A.

In the chimeric protein, the antibody-binding protein may be present at the N-terminal side, the C-terminal side or in the interior of the vesicular stomatitis virus G (VSV-G) protein; however, the antibody-binding protein preferably presents at the N-terminal side of the vesicular stomatitis virus G (VSV-G) protein.

The virus comprising a chimeric protein of an antibody-binding protein and a vesicular stomatitis virus G (VSV-G) protein may comprise a vesicular stomatitis virus G (VSV-G) protein in addition to the chimeric protein. If the virus comprises a vesicular stomatitis virus G (VSV-G) protein in addition to the chimeric protein, the molar ratio of the chimeric protein and the vesicular stomatitis virus G (VSV-G) protein in the virus falls within the range of preferably 1:1 to 1:512, more preferably 1:1 to 1:256, further preferably 1:1 to 1:128, further preferably 1:1 to 1:64 and further preferably 1:2 to 1:64.

If a virus comprises a vesicular stomatitis virus G (VSV-G) protein in addition to the chimeric protein, the virus can be produced by using a plasmid vector which comprises a nucleotide sequence encoding the chimeric protein of an antibody-binding protein and a vesicular stomatitis virus G (VSV-G) protein, in combination with a plasmid vector which does not comprise a nucleotide sequence encoding the antibody-binding protein and comprises a nucleotide sequence encoding the vesicular stomatitis virus G (VSV-G) protein. In this case, the mass ratio of the plasmid vector which does not comprise a nucleotide sequence encoding the antibody-binding protein and comprises a nucleotide sequence encoding the vesicular stomatitis virus G (VSV-G) protein, and the plasmid vector which comprises a nucleotide sequence encoding the chimeric protein of an antibody-binding protein and a vesicular stomatitis virus G (VSV-G) protein, falls within the range of preferably 64:1 to 64:256; for example, the ratio may be 64:2 to 64:256, 64:4 to 64:256, 64:8 to 64:256, 64:16 to 64:256, 64:32 to 64:256; 64:1 to 64:128, 64:1 to 64:64, 64:1 to 64:32; or 64:2 to 64:128, 64:4 to 64:128, 64:8 to 64:128, 64:16 to 64:64.

The chimeric protein can comprise a secretion signal peptide.

As the secretion signal peptide, for example, a VSV-G signal peptide or a signal peptide (a human secretion signal peptide based on the hidden Markov Model) described in, e.g., Biochemical and Biophysical Research Communications 294 (2002) 835-842, can be used.

The chimeric protein may comprise a linker for connecting an antibody-binding protein and the vesicular stomatitis virus G (VSV-G) protein. The linker preferably has a flexible structure. Owing to the flexible structure, the protein acquires movability. In Examples (described later), as a linker, a flexible glycine serine linker is used, which is formed of 15 amino acids constituted of units each consisting of 5 amino acids of 4 glycine residues and 1 serine residue; however, the type of linker is not particularly limited.

The virus comprising a chimeric protein of an antibody-binding protein and a vesicular stomatitis virus G (VSV-G) protein can be produced by the following method.

A method for preparing a retrovirus can include a method of producing a retrovirus by transferring an expression vector (packaging plasmid) having a gag-pol gene; an expression vector having a nucleotide sequence encoding a chimeric protein of an antibody-binding protein and a vesicular stomatitis virus G (VSV-G) protein; and an expression vector having a foreign gene, into a cell having no structural protein of a retrovirus. Alternatively, a method of producing a retrovirus may be employed, by transferring, into a retrovirus packaging cell having a gene encoding a gag-pol gene previously integrated in the chromosome, an expression vector having a nucleotide sequence encoding a chimeric protein of an antibody-binding protein and a vesicular stomatitis virus G (VSV-G) protein; and an expression vector having a foreign gene.

Lentivirus is a virus belonging to the retrovirus family and having many genes other than three essential genes. i.e., gag, pol and env, within the genome. A lentiviral vector is a vector using a lentivirus genome sequence, and growing cells and growth-arresting cells can be infected with the lentiviral vector. Since the foreign gene is inserted into the chromosome of a cell, even if the cell is subcultured, the transgene is stably expressed.

As a lentiviral vector derived from a lentivirus, e.g., HIV-1 (human immunodeficiency virus type 1), HIV-2, simian immunodeficiency virus, feline immunodeficiency virus, bovine immunodeficiency virus, equine infectious anemia virus, caprine arthritisenphalitis virus, jembrana disease virus and visna virus, are known. In order to further produce a virus from three structural proteins, gag, pol and env, a rev gene is required. Rev acts on RNA after transcription to selectively export unspliced gag and gag-pol mRNAs outside the nucleus. The structural protein is translated by the action.

As the expression vector, a plasmid vector can be preferably used. If a lentivirus is produced by using a plasmid vector,
 a plasmid vector (CSIV-CMV-Venus in Examples described later) having a foreign gene;
 a packaging plasmid vector (pLenti-P3A in Examples described later) having a gag gene and a pol gene;
 a packaging plasmid vector (pLenti-P3B in Examples described later) having a rev gene; and
 a plasmid vector having a nucleotide sequence encoding chimeric protein of an antibody-binding protein and a vesicular stomatitis virus G (VSV-G) protein can be used.

The foreign gene of the present invention may be linked under control of an appropriate promoter such as an LTR promoter or a foreign promoter present in a viral vector. As the foreign promoter, any promoter can be used as long as it can be generally used. Examples thereof include CMV (Cytomegalovirus), RSV (Respiratory syncytial virus), SV40 (Simian Virus 40), HSV TK promoter, EF-1 α promoter (Kim et al., Gene 91, p. 217-223 (1990)), CAG promoter (Niwa et al., Gene 108, p. 193-200 (1991)), SR α promoter (Takebe et al. Mol. Cell. Biol. 8, p. 466 (1988)) and β-actin promoter (for example, JP Patent No. 5198747). To efficiently transcribe a foreign gene, other regulatory elements acting in concert with a promoter and a transcription initiation site, such as an enhancer sequence, a terminator sequence and an intron sequence may be present in the vector.

As the foreign gene, any gene can be selected. Examples of the foreign gene include a gene encoding an enzyme or protein involved in a target disease to be treated, T cell receptor gene, a gene encoding a growth factor, a gene encoding antisense RNA, a gene encoding RNA inducing RNA interference (RNAi) and a gene encoding ribozyme. Alternatively, a gene encoding an industrially useful antibody such as a human monoclonal antibody, an enzyme or a physiologically active substance, may be used as the foreign gene. As the gene, cDNA can be used and codon-optimized cDNA can be used.

The virus to be used in the present invention may comprise an appropriate marker gene based on which transgenic cells can be selected. Examples of the marker genes that can be used include drug resistant genes (e.g., neomycin resistant gene) developing resistance of a cell to an antibiotic substance; reporter genes (LacZ (β-galactosidase gene) that can distinguish a transgenic cell based on enzymatic activity or fluorescence; genes encoding a fluorescent protein such as GFP (green fluorescent protein) or an analog thereof; and cell surface marker genes localized in the cell surface. As the cell surface marker gene, a gene lacking a part and/or whole intracellular region and a mutant losing a signal transduction ability may be used.

The plasmid vector comprising a nucleotide sequence encoding the chimeric protein of an antibody-binding protein and a vesicular stomatitis virus G (VSV-G) protein constitutes one aspect of the present invention. The above plasmid vector may comprise an appropriate promoter that can express the chimeric protein. As the promoter, any promoter can be used as long as it is generally used. Examples thereof include CMV (Cytomegalovirus), RSV (Respiratory syncytial virus), SV40 (Simian Virus 40), HSV TK promoter, EF-1 α promoter (Kim et al., Gene 91, p. 217-223 (1990)), CAG promoter (Niwa et al., Gene 108, p. 193-200 (1991)), SR α promoter (Takebe et al., Mol. Cell. Biol. 8, p. 466 (1988)) and β-actin promoter (for example, JP Patent No. 5198747). To efficiently transcribe a foreign gene, other regulatory elements acting in concert with a promoter and a transcription initiation site, such as an enhancer sequence, a terminator sequence, poly A sequence and an intron sequence may be present in the vector.

In the present invention, a virus can be produced within an animal cell by transferring each of the various expression vectors mentioned above into an animal cell (packaging cell). The viruses produced can be collected by collecting the culture supernatant of the animal cell. As the animal cell (packaging cell), e.g., 293T cell and COS-1 cell, can be used.

As the serum to be added to a medium for use in preparation of a virus and infection of a target cell therewith, serum generally used in animal-cell culture can be used. Serum containing no immunoglobulin or serum reduced in immunoglobulin is preferably used. Alternatively, a completely synthesized medium containing no immunoglobulin may be used.

(2) Target Cell and Antibody

In the method for producing a transgenic cell according to the present invention, (i) a virus is contacted with (ii) a target cell and an antibody specific to the target cell, and/or a target cell comprising a membrane antibody to infect the target cell with the virus.

In the method of the present invention, the type of target cell into which a gene is to be transferred is not particularly limited. Examples of the target cell that can be used include stem cells (hematopoietic stem cells, mesenchymal stem cells, embryonic stem cells (e.g., human embryonic stem cells (ES cell)), human induced pluripotent stem cells (iPS cell), hematopoietic cells, mononuclear cells (e.g., peripheral blood mononuclear cells, umbilical cord blood mononuclear cells), germ cells, primordial germ cells, oocytes, oogonia, eggs, spermatocytes, sperms, erythroid progenitor cells, lymphoblasts, mature blood cells, lymphocytes, B cells, T cells, NK cells, NKT cells, macrophages, monocytes, dendritic cells, fibroblasts, neuroblast, nerve cells, endothelial cells, vascular endothelial cells, liver cells, myoblasts, skeletal muscle cells, smooth muscle cells, striated myocytes, cardiomyocytes, cancer cells, myeloma cells and leukemia cells. The target cell may be at least one of human primary cells, human induced pluripotent stem cells (iPS cell), human embryonic stem cells (ES cell), or cells differentiated and induced from these cells. As the preferable target cell, a peripheral blood mononuclear cell, a human B cell or a human T cell is mentioned; however, the target cell is not particularly limited.

The hematopoietic cells obtained from blood and the bone marrow are easily available and methods for culturing and maintaining the cells have been established. Because of this, the hematopoietic cells are suitable for use in the method of the present invention. In particular, if the gene to be transferred is desired to express for a long term, in vivo, pluripotent stem cells (e.g., hematopoietic stem cells and mesenchymal stem cells) and various progenitor cells are suitable as a target cell. When a gene therapy is applied to a treatment for AIDS, cells from the immune system such as CD4 positive T cells and progenitor cells thereof are suitably used as a target cell.

A kit comprising a target cell selected from human primary cells, human induced pluripotent stem cells (iPS cell), human embryonic stem cells (ES cell) and human mesenchymal stem cells, and an antibody specific to the target cell is useful as a kit for use in the method for producing a transgenic cell according to the present invention.

In the present invention, (i) a virus is contacted with (ii) a target cell and an antibody specific to the target cell, and/or a target cell comprising a membrane antibody, in vitro.

As the antibody specific to a target cell, an antibody specific to an antigen present in a cell surface can be used. Examples of the antigen present in a cell surface include, but are not limited to, the followings.

Cell surface differentiation antigens (antigen classified in CD (Cluster of Designation));

Class I and class II major histocompatible antigens;

receptors for cytokines and growth hormones (for example, brain-derived neurotrophic factor (BDNF), ciliary neurotrophic factor (CTNF), colony stimulating factor, endothelial growth factor, epidermal growth factor, fibroblast growth factor, glial cell-derived neurotrophic factor, glial cell growth factor, gro-beta/mip 2, hepatocyte growth factor, insulin-like growth factor, interferons (α-IFN, β-IFN, γ-IFN, consensus IFN), interleukins (IL-1, IL-2, IL-3, IL-4, IL-5, IL-6, IL-7, IL-8, IL-9, IL-10, IL-11, IL-12, IL-13, IL-14), keratinocyte growth factor, leukemia inhibitory factor, macrophage/monocyte chemotactic activator, nerve growth factor, neutrophil-activated protein 2, platelet-derived growth factor, stem cell factor, transforming growth factor, tumor necrosis factor and vascular endothelial growth factor);

cell adhesion molecules;

molecules for transporting a metabolite such as an amino acid;

antigen receptors of B- and T-lymphocytes; and lipoprotein receptors.

Examples of a combination of a predetermined target cell and a cell surface marker specific to the predetermined target cell are shown below.

Note that, other than the examples below, examples of the combination of a predetermined target cell and a cell surface marker specific to the predetermined target can be searched from BioGPS (http://biogps.org/) or UniProt (http://www.uniprot.org/).

Pluripotent stem cells (ESCs and iPSCs): SSEA-4, SSEA-3, TRA-1-81, TRA-1-60

Hematopoietic stem cells (Hematopoietic Stem Cells: HSCs): CD34, CD49, CD90/Thy 1

Multipotent progenitor cells (MPP): CD34

Common lymphoid progenitor cells (CLP): CD34, CD38, CD10, CD45RA

Common myeloid progenitor cells (CMP): CD34, CD38, CD135

Megakaryocyte/erythroid progenitor cells (MEP): CD34, CD38

Granulocytes/macrophage progenitor cells (GMP): CD34, CD38, CD45RA, CD123, CD135

NK cells: CD56, CD94, NKp46

T cells: CD3

B cells: CD19

Monocytes: CD14

Macrophages: CD11b, CD68, CD163

Dendritic cells: CD11c, HLA-DR

Neutrophils: CD11b, CD16, CD18, CD32, CD44, CD55

Eosinophils: CD45, CD125, CD193, F4/80, Siglec-8

Basophils: CD22, CD45low, CD123

Mast cells: CD32, CD33, CD117, CD203c, FcεRI

Megakaryocytes: CD41b, CD42a, CD42b, CD61

Mesenchymal stem cells (MSC): CD44, CD73, CD90, CD105, CD146, CD271

Neural stem cells (Neural Stem Cell: NSC): CD15mid, CD24, CD184

Neurons: CD15low, CD24

Tumors: CD15, CD24, CD34, CD44, CD45, CD49f, CD166, CD326, CD338, Her-2/Neu, Lgr5

In the present invention, as the antigen present on a cell surface, a differentiated antigen is used. Due to this, infection specific to a predetermined type of cell can be made.

In an example of the present invention, the target cell is a human T cell; and the antibody specific to the target cell is at least one selected from an anti-human CD3 antibody, an anti-human CD8a antibody and an anti-human CD11a antibody.

In another embodiment of the present invention, the target cell is a human B cell; and the target cell is contacted with the virus as mentioned above in vitro in the presence of at least one selected from a stimulation via IL-4, ODN 2006, CD40 receptor and a stimulation via a BAFF receptor. In this manner, cell growth can be induced or cells can be activated.

In still another embodiment of the present invention, the target cell is a human mesenchymal stem cell; and an antibody specific to the target cell is an anti-human CD90 antibody.

(3) Viral Infection to Target Cell

According to the present invention, a desired gene can be transferred into a target cell. More specifically, the method for producing a transgenic cell according to the present invention can be used as a gene transfer method.

In the present invention, a virus can be contacted with a target cell in vitro to infect the cell with the virus. The transferred gene can be expressed by culturing the target cell infected with the virus in conditions customarily employed. In other words, the target cell is cultured in a culture solution to obtain a protein encoded by the foreign gene transferred thereinto. Alternatively, the target cell transduced in vitro can be transplanted to a subject.

A transgenic cell obtained by the method for producing a transgenic cell according to the present invention, in other words, a transgenic cell infected with the virus of the present invention falls within the scope of the present invention.

(4) Gene Therapy

The virus described in the specification is useful as an active ingredient of a gene therapeutic agent. More specifically, according to the present invention, there is provided a gene therapeutic agent comprising a virus as described in the specification. To describe more specifically, there is provided a gene therapeutic agent having a virus comprising: a chimeric protein of an antibody-binding protein and a vesicular stomatitis virus G (VSV-G) protein; and a foreign gene, in which the antibody-binding protein comprises an IgG-binding domain of protein L and/or 3 or more IgG-binding domains of protein A. The gene therapy of the present invention may comprise other components such as a pharmaceutically acceptable carrier or a diluent, in combination with the virus serving as an active ingredient. A gene therapy comprising administering the gene therapeutic agent comprising a virus as described in the specification to a subject (e.g., patient) falls within the scope of the present invention.

In the present invention, the gene therapeutic agent of the present invention, if desired, together with an antibody, can be directly administered to a subject. The administration route to a subject is not particularly limited and any administration route can be used as long as a virus can be in contact with a target cell. For example, intravenous administration is appropriate for a target cell of the liver, spleen, kidney, heart, circulatory system or hematopoietic system. A virus can be administered through a catheter injected in the artery or vein leading to a target organ. According to this method, local administration can be made. A virus can be administered by inhalation if a target cell is present in the respiratory system.

The dose of the gene therapeutic agent of the present invention can be appropriately selected by those skilled in the art depending on the type of foreign gene comprised in the virus, type of disease to be treated, administration site, severity, and the age, body weight, sex and health condition of the patient. The titer of a virus is preferably larger than $10^5$ cfu/ml, further preferably $10^6$ cfu/ml, further preferably $10^7$ cfu/ml, further preferably $10^8$ cfu/ml, further preferably $10^9$ cfu/ml, further preferably $10^{10}$ cfu/ml and further preferably $10^{11}$ cfu/ml. The virus of the present invention is physically highly tolerant and can be easily concentrated by ultra-centrifugation.

When the gene therapeutic agent of the present invention is administered to a patient, the gene is transferred into predetermined cells in a target region and integrated into the chromosome of the cells. In this manner, a foreign gene can be stably expressed. Using the gene transfer method, a gene therapy can be applied to various diseases of a mammal including a primate such as a human.

For example, a gene therapy targeting CD4 positive T cells can be carried out by the following procedure. For example, the bone marrow tissue, peripheral blood or cord blood is taken from a donor as a material containing CD4 positive T cells. The material taken may be directly used for gene transfer; however, the material is subjected to, e.g., density gradient centrifugation, to prepare a mononuclear cell fraction. Further, operations such as purification of cells based on a CD4 molecule as an index, removal of CD8 positive T cells and/or monocytes, and culture in order to increase the number of CD4 positive T cells, can be carried out. The cell population, if necessary, is preliminarily stimulated with, for example, CD3 ligand, CD28 ligand or IL-2, and thereafter, infected with a virus having a foreign gene in accordance with the method of the present invention. The transgenic cells obtained by the above operation can be transplanted to a recipient by, for example, intravenous administration. The recipient is preferably a donor him/herself, however, allogeneic transplantation can be made.

As a gene therapy targeting hematopoietic stem cells, a gene therapy making up for a defective gene or an abnormal gene of a patient is known. Examples thereof include a gene therapy for ADA deficiency and Gaucher's disease. Other than these, transferring a drug resistant gene into hematopoietic stem cells in order to reduce damage of hematopoietic cells by a chemotherapeutic agent used for treating cancer and leukemia, may be mentioned.

As a cancer gene therapy, a method of transferring a gene encoding a T cell receptor recognizing a tumor antigen to provide cytotoxic activity specific to cancer cells expressing the antigen to lymphocytes has been studied. Further, an attempt to treat AIDS by a gene therapy has been made. In this case, it is considered to transfer a gene encoding a nucleic acid molecule (single strand specific endoribonuclease, an antisense nucleic acid, ribozyme), which inhibits replication or gene expression of HIV, to T cells such as CD4 positive T cells which is infected with HIV causing AIDS.

EXAMPLES

Now, the present invention will be more specifically described by way of Examples; however, the present invention is not limited by these Examples. Genes were manipulated in accordance with a leading method unless otherwise specified (J. Sambrook, E. F. Fritsch, t. Maniatis; Molecular Cloning, A Laboratory Manual, 2nd Ed, Cold Spring Harbor Laboratory). Cells were cultured in accordance with a leading method unless otherwise specified ("Cell Culture Lab Manual" Springer Verlag Tokyo, first edition, edited by Hideki Koyama). When a trade name is described, unless otherwise specified, experiments were carried out in accordance with the instructions of the attached protocols.

(Example 1) Preparation of Expression Vector for the Chimeric Envelope Protein Having an Antibody-Binding Protein and VSV-G (Vesicular Stomatitis Virus G) Protein pVSV-G (Clontech Laboratories, Inc) was partially digested with XohoI (two or more digestion sites are present; however, the plasmid was treated such that all sites were not digested), and then the ends were converted into the blunt ends. Electrophoresis was performed, a band of about 6500 bp was recovered, and subjected to purification using MinElute Gel Extraction Kit (QIAGEN). Through Ligation using DNA Ligation Kit Ver. 2.1 (Takara Bio Inc.), a plasmid (pVSV-G (back XhoI to PvuI)) was obtained, in which an XhoI site downstream of ORF of VSV-G was converted to a PvuI site. The sequences represented by SEQ ID NO: 1 and SEQ ID NO: 2 were totally synthesized, digested with XhoI and SwaI, and electrophoresed. Bands of about 550 bp band and about 560 bp band were separately recovered and subjected to purification. The pVSV-G (back XhoI to PvuI) was digested with XhoI and SwaI, dephosphorylated and electrophoresed. A band of about 6400 bp was recovered and subjected to purification. The fragments derived from the sequences of SEQ ID NO: 1 and SEQ ID NO: 2 were separately ligated with the fragment derived from pVSV-G (back XhoI to PvuI) to produce plasmids pPA2d-VSV-G and pPG2d-VSV-G (FIG. 1). *Escherichia coli* JM109 (TOYOBO Co., Ltd) was transformed with the plasmid ligated and cultured in 2×YT agar medium containing carbenicillin in a final concentration of 100 μg/ml and 2×YT medium, and then, sequence analysis and plasmid preparation were carried out. The plasmid was purified by use of QIAprep Spin Miniprep Kit (QIAGEN) and NucleoBond Xtra Midi (Takara Bio Inc).

pCI-neo (Promega Corporation) was digested with ClaI and electrophoresed. A band of about 3500 bp was recovered and subjected to purification and ligation. In this manner, pCI was prepared. pCI was sufficiently digested with EcoRI (a plurality of digestion sites are present and the vector was treated so as to digest all sites were digested), dephosphorylated and electrophoresed. A band of about 3500 bp was recovered and subjected to purification. pVSV-G was sufficiently digested with EcoRI and electrophoresed. A band of about 2800 bp was recovered and subjected to purification. The fragment derived from pCI and the fragment derived from pVSV-G were ligated. A plasmid having an initiation codon near the CMV promoter was selected to prepare an expression vector pCI-VSV-G (FIG. 1). pCI-VSV-G was digested with XhoI and SwaI, dephosphorylated and electrophoresed. A band of about 5000 bp was recovered and subjected to purification. The fragments represented by SEQ ID NO: 3 and SEQ ID NO: 4 were totally synthesized, digested with XhoI and SwaI and electrophoresed. Bands of about 180 bp and about 220 bp were separately recovered and subjected to purification. The fragment derived from pCI-VSV-G was ligated separately with the fragments derived from the fragments represented by SEQ ID NO: 3 and SEQ ID NO: 4 to prepare pCI-SP-VSV-G and pCI-SP-GS2-VSV-G (FIG. 1). HMM-38 signal peptide was used with reference to Biochem Biophys Res Commun. 2002 Jun. 21; 294 (4): 835-42.

pCI-SP-GS2-VSV-G was digested with NaeI, dephosphorylated and electrophoresed. A band of about 5700 bp was recovered and subjected to purification. The fragments represented by SEQ ID NO: 5, SEQ ID NO: 6 and SEQ ID NO: 7 were totally synthesized and digested with EheI and NaeI; ScaI and SacI; and MlyI and NaeI, respectively, and then electrophoresed. Bands of about 500 bp, about 580 bp and about 620 bp bands were recovered respectively and subjected to purification. The fragment derived from pCI-SP-GS2 VSV-G and the fragments derived from SEQ ID NO: 5, SEQ ID NO: 6 and SEQ ID NO: 7 were separately ligated to prepare expression vectors of pCI-SP-PA3d-GS2-VSV-G, pCI-SP-PG3d-GS2-VSV-G and pCI-SP-PL3d-GS2-VSV-G (FIG. 1). The fragment(s) derived from SEQ ID NO: 5 and/or SEQ ID NO: 7 were subjected to ligation for preparing linear DNA. A desired band was recovered and subjected to purification. The purified fragment and was ligated to the fragment derived from pCI-SP-GS2-VSV-G. Fragments having an insert placed in a right direction of the promoter were selected. In this manner, pCI-SP-PA6d-VSV-G, pCI-SP-PA9d-VSV-G, pCI-SP-PA12d-VSV-G, pCI-SP-PL6d-VSV-G, pCI-SP-PL9d-VSV-G, pCI-SP-PL12d-VSV-G, pCI-SP-PA3d-PL3d-VSV-G, and pCI-SP-PL3d-PA3d-VSV-G were obtained (FIG. 2).

(Example 2) Preparation of Vector Plasmid

As a lentiviral vector plasmid for measuring efficiency of infection of cells, CSIV-CMV-Venus was used. CSIV-CMV-MCS-IRES2-Venus (Cancer Sci. 2014 April; 1054: 402-8) was partially digested with BalI, and then digested with Aor51HL and electrophoresed. A band of about 9030 bp was recovered and subjected to purification and ligation, to prepare CSIV-CMV-Venus. As a packaging plasmid for use in preparing a lentivirus, pLenti-P3A (packaging plasmid for gag and pol) and pLenti-P3B (packaging plasmid for rev) of 3rd Generation pLenti-Combo Mix (Applied Biological Materials Inc.) were used. As a packaging plasmid for env, the packaging plasmid described in Example 1 was used.

pMSCV-bact-Venus-wpre was used as a retroviral vector plasmid for measuring efficiency of infection of cells. pMSCV-neo-bact-fEPO-wpre (JP Patent No. 5198747) was digested with NotI and electrophoresed. A band of about 6200 bp was recovered and subjected to purification and ligation, to prepare pMSCV-bact-fEPO-wpre. pMSCV-bact-fEPO-wpre was digested with SalI and HindIII, dephosphorylated and electrophoresed. A band of about 5050 bp was recovered and subjected to purification. Amplification was carried out by PCR using CSIV-CMV-MCS-IRES2-Venus as a template and SEQ ID NO: 8 and SEQ ID NO: 9 as primers. The obtained fragments were subjected to purification by MinElute PCR Purification Kit (QIAGEN), recovered, digested with SalI and HindIII and electrophoresed. A band of about 790 bp was recovered and subjected to purification. The fragment derived from pMSCV-bact-fEPO-wpre and the fragment derived from CSIV-CMV-MCS-IRES2-Venus were ligated to prepare pMSCV-bact-Venus-wpre.

(Example 3) Preparation of Feeder Cells

For culturing human B cells, feeder cells which express a human CD40 ligand and human BAFF were prepared.

The human CD40 ligand (see, for example, Eur J Immunol. 1992 December; 22 (12): 3191-4, and, EMBO J. 11 (12), 4313-4321 (1992), NCBI Reference Sequence: NM_000074), and human BAFF (for example, J Exp Med. 1999 Jun. 7; 189 (11): 1747-56, Science. 1999 Jul. 9; 285 (5425): 260-3, NCBI Reference Sequence: NM_006573) were totally synthesized based on e.g., information in documents. pMSCV-bact-fEPO-wpre was digested with NotI and ClaI, dephosphorylated and electrophoresed. A band of about 5000 bp was recovered and subjected to purification. Single strand DNAs, i.e., the fragments of SEQ ID NO: 10 and SEQ ID NO: 11 phosphorylated at the 5' end, were synthesized, mixed, treated with heat and gently cooled to obtain a double stranded DNA, which was ligated to the fragment derived from pMSCV-bact-fEPO-wpre to prepare pMSCV-MCS-wpre. pMSCV-MCS-wpre was digested with NotI and XhoI, dephosphorylated and electrophoresed. A band of about 5100 bp was recovered and subjected to purification. CSIV-CMV-MCS-IRES2-Venus was digested with NotI and XhoI and electrophoresed. A band of about 1300 bp was recovered and subjected to purification. The fragment derived from pMSCV-MCS-wpre and the fragment derived from CSIV-CMV-MCS-IRES2-Venus were ligated to prepare pMSCV-IRES2-Venus-wpre. pMSCV-IRES2-Venus-wpre was digested with NotI and EcoRI, dephosphorylated and electrophoresed. A band of about 5000 bp was recovered and subjected to purification. Amplification was carried out by PCR using CSIV-CMV-MCS-IRES2-Venus as a template and SEQ ID NO: 12 and SEQ ID NO: 13 as the primers. The amplified product was electrophoresed. A band of about 1300 bp was recovered and subjected to purification. Amplification was carried out by PCR using human CD40 ligand cDNA synthesized as a template and SEQ ID NO: 14 and SEQ ID NO: 15 as the primers. The amplified product was electrophoresed. A band of about 830 bp was recovered and subjected to purification. Amplification was carried out by PCR using the band of about 1300 bp and a band of about 830 bp as templates and SEQ ID NO: 12 and SEQ ID NO: 15 as primers. The amplified product was purified, digested with NotI and EcoRI and electrophoresed. A band of about 1400 bp was recovered, and subjected to purification and ligation with the fragment derived from pMSCV-IRES2-Venus-wpre to prepare pMSCV-IRES2-CD40L-wpre. pMSCV-IRES2-CD40L-wpre was digested with NotI, dephosphorylated and electrophoresed. A band of about 6400 bp was recovered and subjected to purification. Amplification was carried out by PCR using human BAFFcDNA synthesized as a template and SEQ ID NO: 16 and SEQ ID NO: 17 as primers. An amplified product was purified, digested with NotI and electrophoresed. A band of about 900 bp was recovered and subjected to purification and ligation with the fragment derived from pMSCV-IRES2-CD40L-wpre. A plasmid having an initiation codon for human BAFF inserted near the 5'LTR promoter was selected to prepare pMSCV-BAFF-IRES2-CD40L-wpre. A retroviral vector was prepared in accordance with JP Patent No. 5198747 and Balb/c 3T3 cells were infected with retroviral vector. Expression of BAFF was evaluated by a flow cytometer using Human BAFF Quantikine ELISA Kit (R&D Systems) and expression of CD40L was evaluated by FITC anti-human CD154 Antibody (BioLegend). Based on expressions of BAFF and CD40L, cloning was performed to obtain h40LB.

(Example 4) Preparation of sCD40L and sBAFF

E. coli HST04 Competent Cells (Takara Bio Inc) were transformed with pIRES (Takara Bio Inc) and cultured in 2×YT medium containing carbenicillin in a final concentration of 100 μg/ml to prepare a plasmid. pIRES was digested with ClaI and electrophoresed. A band of about 4100 bp was recovered and subjected to purification and ligation to prepare dpIRES. dpIRES was completely digested with SmaI, dephosphorylated and electrophoresed. A band of about 4100 bp was recovered and subjected to purification. Amplification was carried out by PCR using pLVSIN-EF1α Pur (Takara Bio Inc) as a template and SEQ ID NO: 18 and SEQ ID NO: 19 as primers. An amplified fragment was purified, recovered, phosphorylated and electrophoresed. A band of about 600 bp was recovered and subjected to purification. The fragment derived from dpIRES and the fragment derived from pLVSIN-EF1α Pur were ligated. A plasmid having an initiation codon near IRES was selected to prepare dpIRES-Pur. dpIRES-Pur was digested with XhoI and MluI, dephosphorylated and electrophoresed. A band of about 4700 bp was recovered and subjected to purification. Single strand DNAs, the fragments of SEQ ID NO: 20 and SEQ ID NO: 21 phosphorylated at the 5' end, were synthesized, mixed, treated with heat and gently cooled to obtain a double stranded DNA, which was ligated to the fragment derived from dpIRES-Pur to prepare dpCMV-MCS-IRES-Pur. SEQ ID NO: 22 was totally synthesized, digested with NheI and EcoI and electrophoresed. A band of about 900 bp was recovered and subjected to purification. dpCMV-MCS-IRES-Pur was digested with NheI and EcoI, dephosphorylated and electrophoresed. A band of about 4700 bp was recovered and subjected to purification. The fragment derived from SEQ ID NO: 22 and the fragment derived from dpCMV-MCS-IRES-Pur were ligated to prepare dpCMV-sCD40L-IRES-Pur. Then, 293T cells were transformed by using dpCMV-sCD40L IRES-Pur. Cells stably expressed were selected in the presence of puromycin and 293T (sCD40L) was cloned. Subsequently, 293T (sCD40L) was cultured in 293 SFM II (Thermo Fisher Scientific) containing 2× GlutaMAX (Thermo Fisher Scientific) and the supernatant was purified with Strep-Tactin Sepharose Column (IBA). The purified solution eluted was replaced with PBS by use of Vivaspin Turbo 15 (MWCO: 10,000) (Sartorius) (refining sCD40L). SEQ ID NO: 23 was totally synthesized and subjected to the same experiment to obtain purified sBAFF. CD40L and BAFF each are a membrane protein (homotrimer, type II) belonging to the TNF super family and can be produced by fusing extracellular domains of CD40L and BAFF separately with a coiled coil sequence (Philos Trans R Soc Lond B Biol Sci. 1995 Apr. 29; 348 (1323): 81-8) represented by SEQ ID NO: 24, as an active trimer protein.

(Example 5) Separation of Cells from Blood

Use of blood was approved by the ethics committee in house. After informed consent was obtained, blood was used. Blood was taken by a doctor/nurse in Terumo blood bag CPDA (Terumo Corporation) and subjected to mononuclear cell separation using Lymphoprep Tube (tube size: 50 mL) (Alere Technologies AS) to obtain PBMC. To this, biotin-anti-human CD2 antibody (BioLegend) and biotin-anti-human CD235a antibody (eBioscience) were reacted in accordance with a customary method. CD2- and CD235-negative cells were recovered by use of Streptavidin-Particle Plus-DM, BD IMagnet (BD Bioscience Pharmingen). With the cells, a PE/Cy7 anti-human CD19 antibody was reacted in accordance with a customary method and CD19 positive cells were sorted by ARIAIII (BD Biosciences) to obtain human B cells. The B cells were cryopreserved with CELL-BANKER2 (Takara Bio Inc) as frozen B cells. The blood taken above was separated by RosetteSep human B cell (STEMCELL Technologies) to obtain B cells and used as fresh B cells.

(Example 6) Evaluation of pVSV-G, pCI-VSV-G and pCI-SP-VSV-G

First, 293T cells were seeded on a collagen coated 24-well plate so as to be present in the number of $6\times10^5$ cells and cultured in Advanced RPMI 1640 culture medium (containing 2× GlutaMAX and 100% FBS) (Thermo Fisher Scientific) overnight. On the following day, the culture medium was exchanged with 0.5 mL of Advanced RPMI 1640 culture medium (containing 2× GlutaMAX and 2% FBS). Using Lipofectamine 3000 Reagent (Thermo Fisher Scientific), CSIV-CMV-Venus (0.5 μg), pLenti-P3A (0.5 μg), pLenti-P3B (0.5 μg) and an envelope protein expression vector (pVSV-G, pCI-VSV-G, pCI-SP-VSV-G) were transfected. Experiment was carried out in the range of 2 μg to 1/64 μg of the envelope protein expression vector. Four hours after transfection, the medium was exchanged with 2 mL of Advanced RPMI 1640 culture medium (containing 2× GlutaMAX and 2% FBS) and culture was carried out for two days to prepare a lentiviral vector. The lentiviral vector prepared was subjected filtration by a 0.8 μm-filter to obtain a viral supernatant stock solution. The stock solution (1 mL) was added to the 24-well plate to which 293T cells were seeded in the number of $2 \times 10^5$ cells and infected overnight. On the following day, the medium was exchanged. Two days after infection, cells were removed by Accumax (Innovative Cell Technologies), stained with a propidium iodide solution (SIGMA) and analyzed by a flow cytometer. Titer (TU/ml) was calculated in accordance with the expression:

Number of cells at the time of infection ($2 \times 10^5$)× living cells Venus positive/total number of living cells.

The evaluation results on the relationship between the VSV-G vector concentration and the titer are shown in FIG. 3. Virus can be produced by using any one of VSV-G vectors; however optimal vector concentrations varied. This is presumed because the expression level of VSV-G varies among the vectors: pCI-VSV-G<pCI-SP-VSV-G<pVSV-G. The virus titers increased in the order of pVSV-G (1/16 μg/24-well plate), pCI-SP-VSV-G (½ μg/24-well plate) and pCI-VSV-G (1 μg/24-well plate). It is estimated that the expression level of pCI-VSV-G is about 1/16 as small as pVSV-G; and the expression level of pCI-SP-VSV-G is 1/8 as small as pVSV-G.

(Example 7) Evaluation of Expression Vector for the Chimeric Envelope Protein of an Antibody-Binding Protein (Protein A: PA, Protein G: PG, Protein L: PL) and VSV-G (Vesicular Stomatitis Virus G) Protein Preparation of a lentiviral vector and titer measurement were carried out in the same manner as in Example 6 (FIG. 4). Note that the envelope protein expression vectors were used in quantitative ratios shown in Table 1. Infection to B cells was examined by centrifuging cryopreserved B cells so as to obtain $1.25 \times 10^5$ cells, suspended with 1 mL of a viral supernatant (containing IL-4 50 ng/mL, IL-2 25 U/mL, sCD40L 400 ng/mL, sBAFF 100 ng/mL), seeded in a 24-well plate and infected overnight. On the following day, the cells were centrifuged and suspended in Advanced RPMI 1640 (2% FBS, IL-4 (50 ng/mL), IL-2 (25 U/mL), sCD40L (400 ng/mL), sBAFF (100 ng/mL), A286982 2 μM) and continued to culture. Three days later, the cells were centrifuged, suspended in Advanced RPMI 1640 (2% FBS, IL-21 (10 ng/mL), IL-2 (25 U/mL), sCD40L (400 ng/mL), sBAFF (100 ng/mL), A286982 2 μM) and continued to culture. Three days later, the cells were stained with a propidium iodide solution and analyzed by a flow cytometer, and then, the proportion (%) of Venus positive cells was calculated. The results are shown in FIG. 4. The efficiency of infection of B cells is remarkably increased by using the expression vector for a chimeric envelope protein of PA or PL and VSV-G protein. In the expression vector for a chimeric envelope protein of PG and VSV-G protein, the efficiency of infection of B cells decreased from that of pVSV-G. The efficiency of infection per titer increased by about 1.8 times by increasing the number of domains in PA from 2 to 3.

TABLE 1

| Label of graph FIG. 4 | pVSV-G (μg) | Expression vector for chimeric envelope protein | (μg) |
|---|---|---|---|
| pVSV-G | 0.500 | — | — |
| pPA2d-VSV-G | 0.375 | pPA2d-VSV-G | 0.125 |
| pPG2d-VSV-G | 0.375 | pPG2d-VSV-G | 0.125 |
| pCI-SP-PA3d-GS2-VSV-G | 0.375 | pCI-SP-PA3d-GS2-VSV-G | 0.250 |
| pCI-SP-PG3d-GS2-VSV-G | 0.375 | pCI-SP-PG3d-GS2-VSV-G | 0.250 |
| pCI-SP-PL3d-GS2-VSV-G | 0.375 | pCI-SP-PL3d-GS2-VSV-G | 0.250 |

(Example 8) Evaluation of the Number of Domains of an Antibody-Binding Protein and Efficiency of Infection First, 293T cells were seeded in a collagen coated 12-well plate so as to be present in the number of $1.1 \times 10^6$ cells and cultured in Advanced RPMI1640 culture medium (containing 2× GlutaMAX and 10% FBS) overnight. On the following day, the culture medium was exchanged with 1 mL of Advanced RPMI 1640 culture medium (containing 2× GlutaMAX and 2% FBS) (ultra-low IgG) (Thermo Fisher Scientific). Using Lipofectamine 3000 Reagent, CSIV-CMV-Venus (1 μg), pLenti-P3A (1 μg), pLenti-P3B (1 μg), pVSV-G (0.125 μg) and an expression vector for the chimeric envelope protein (0.25 μg) were transfected. Four hours after transfection, the culture medium was exchanged with 5 mL of Advanced RPMI 1640 culture medium (containing 2× GlutaMAX and 2% FBS (ultra-low IgG)) and culture was carried out for two days to prepare a lentiviral vector. The lentiviral vector prepared was subjected filtration by a 0.8 μm-filter to obtain a viral supernatant stock solution. In a 24-well plate, 293T cells were seeded in the number of $1.3 \times 10^5$ cells and cultured in 1 mL of Advanced DMEM culture medium (Thermo Fisher Scientific) (containing 2×GlutaMAX and 2% FBS). To this, 0.2 mL of the viral supernatant stock solution was added and infected overnight. On the following day, the medium was exchanged. Five days after infection, cells were removed by Accumax, stained with a propidium iodide solution and analyzed by a flow cytometer. Titer (TU/ml) was calculated in accordance with the expression:

Number of cells at the time of infection ($1.3 \times 10^5$)× living cells Venus positive/total number of living cells.

The evaluation results on the relationship between the number of domains of an antibody-binding protein and the titer are shown in FIG. 5. The cryopreserved B cells were cultured in Advanced RPMI1640 (containing 2% FBS (ultra-low IgG), IL-4 (50 ng/mL), IL-2 (25 U/mL), sCD40L (400 ng/mL), sBAFF (100 ng/mL), A286982 2 μM) for 2 days culture. The cultured cells were centrifuged. The viral supernatant stock solution (1 mL) was added to 5000 B cells to cause viral infection of B cells. Two hours later, centrifugation was carried out and the B cells were seeded on feeder cells (h40LB seeded in a 24-well plate so as to be present in the number of $1 \times 10^5$ cells on the previous day) and cultured in Advanced RPMI1640 (containing 2% FBS, L-21 (10 ng/mL), IL-2 (25 U/mL)). Five days later, cells were removed by Accutase (Innovative Cell Technologies) and centrifuged. The cells, with which Alexa Fluor 647 anti-human CD19 antibody was reacted in accordance with a customary method, were stained with a propidium iodide solution and analyzed by a flow cytometer. CD19 positive cells were regarded as B cells and the proportion (%) of Venus positive B cells in living B cells was calculated. The evaluation results on number of domains of an antibody-binding protein and efficiency of infection of B cells are shown in FIG. 5. In pVSV-G, efficiency of infection was less than 1%; however, in the case of the chimeric envelope protein regardless of the number of domains, efficiency of infection was 6% or more. Even if the case where PL and PA are used in combination, the efficiency of infection of the B cells was 7% or more. In either case of PA and PL, the efficiency of infection of the B cells was higher in 6 to 12 domains than in 3 domains.

(Example 9) Evaluation of the Ratio of VSV-G Vector and Expression Vector for the Chimeric Envelope Protein First, 293T cells were seeded on a collagen coated 24-well plate so as to be present in the number of $6\times10^5$ cells and cultured in Advanced DMEM culture medium (containing 2× GlutaMAX and 10% FBS), overnight. On the following day, the culture medium was exchanged with 0.5 mL of Advanced DMEM culture medium (containing 2× GlutaMAX, 2% FBS (ultra-low IgG) and 10 mM HEPES (Thermo Fisher Scientific)). Using Lipofectamine 3000 Reagent (Thermo Fisher Scientific), CSIV-CMV-Venus (0.5 µg), pLenti-P3A (0.5 µg), pLenti-P3B (0.5 µg) and an envelope plasmid were transfected in quantitative ratios shown in Tables 2, 3 and 4. Four hours from transfection, the medium was exchanged with 2 mL of Advanced DMEM culture medium (containing 2× GlutaMAX, 2% FBS (ultra-low IgG) and 10 mM HEPES) and culture was carried out for two days to prepare a lentiviral vector. The lentiviral vector prepared was subjected filtration by a 0.8 µm-filter to obtain a viral supernatant stock solution. The stock solution (10 µL) was added in a 24-well plate where 293T cells were seeded in the number of $5\times10^5$ cells and culture was carried out overnight in 2 mL Advanced DMEM culture medium (containing 2× GlutaMAX and 2% FBS) for infection. On the following day, the medium was exchanged. Two days after infection, cells were removed by Accumax, stained with a propidium iodide solution and analyzed by a flow cytometer. Titer (TU/ml) was calculated in accordance with the expression:

Number of cells at the time of infection $(5\times10^5)\times$ living cells Venus positive/total number of living cells.

The results of Tables 2, 3 and 4 are shown in FIGS. 6, 7 and 8. Frozen B cells were centrifuged so as to obtain $5\times10^4$, suspended in 1 mL of the viral supernatant fluid (containing IL-4 (50 ng/mL), IL-2 (25 U/mL), sCD40L (400 ng/mL), sBAFF (100 ng/mL)), seeded in a 24-well plate and infected overnight. This culture was centrifuged and B cells were seeded on feeder cells (h40LB seeded in a 24-well plate so as to be present in the number of $1\times10^5$ cells on the previous day) and cultured in Advanced RPMI1640 (containing 2% FBS (ultra-low IgG), IL-21 (10 ng/mL), IL-2 (25 U/mL)). Five days later, cells were removed by Accutase and centrifuged. The cells, with which Alexa Fluor 647 anti-human CD19 antibody and Brilliant Violet 421 anti-mouse H-2Kd antibody were reacted in accordance with a customary method, were stained with a propidium iodide solution and analyzed by a flow cytometer. Human CD19 positive cells and mouse H-2Kd negative cells were regarded as B cells and the proportion (%) of Venus positive B cells in living B cells was calculated. The results of Tables 2, 3 and 4 are shown in FIGS. 6, 7 and 8. From FIG. 6, it is found that as the ratio of the chimeric envelope vector increases, the virus titer tends to decrease. In contrast, infection to B cells reached a maximum at a ratio of pVSV-G:pCI-SP-PL6d-VSV-G of 64:32. From the results of Example 6 (FIG. 3), since pCI-SP-VSV-G is about ⅛ as small as that of pVSV-G, the efficiency of infection of B cells is estimated to be high at a ratio of VSV-G protein:chimeric envelope protein of about 16:1 in a viral vector. The ratio of pVSV-G and chimeric envelope vector were more specifically checked as shown in FIG. 7. The efficiency of infection of B cells reached a maximum at a ratio of 5:5 of the ratios of pVSV-G:pCI-SP-PA6d-VSV-G and at a ratio of 5:4 of the ratios of pVSV-G:pCI-SP-PL6d-VSV-G. With respect to the ratio of pVSV-G:pCI-SP-PA6d-VSV-G, there is a possibility that the proportion of pCI-SP-PA6d-VSV-G may be even higher. The ratio of pCI-SP-VSV-G and the chimeric envelope vector was checked as shown in FIG. 8. The efficiency of infection of B cells reached a maximum at a ratio of 16:8 of the ratios of pCI-SP-VSV-G:pCI-SP-PA6d-VSV-G, and at a ratio of 16:2 of the ratios of pCI-SP-VSV-G:pCI-SP-PL6d-VSV-G. In pCI-SP-PA6d-VSV-G, a large amount of vector is required compared to pCI-SP-PL6d-VSV-G.

TABLE 2

| Label of graph FIG. 6 | pVSV-G (ng) | pCI-SP-PL6d-VSV-G (ng) |
| --- | --- | --- |
| 64:0 | 500 | 0 |
| 64:1 | 500 | 7.8 |
| 64:2 | 500 | 15.6 |
| 64:4 | 500 | 31.2 |
| 64:8 | 500 | 62.5 |
| 64:16 | 500 | 125 |
| 64:32 | 500 | 250 |
| 64:64 | 500 | 500 |
| 64:128 | 500 | 1000 |
| 64:256 | 500 | 2000 |

TABLE 3

| Label of graph FIG. 7 | pVSV-G (ng) | pCI-SP-PA6d-VSV-G or pCI-SP-PL6d-VSV-G (ng) |
| --- | --- | --- |
| 5:0 | 125 | 0 |
| 5:1 | 125 | 25 |
| 5:2 | 125 | 50 |
| 5:3 | 125 | 75 |
| 5:4 | 125 | 100 |
| 5:5 | 125 | 125 |

TABLE 4

| Label of graph FIG. 8 | pCI-SP-VSV-G (ng) | pCI-SP-PA6d-VSV-G or pCI-SP-PL6d-VSV-G (ng) |
| --- | --- | --- |
| 16:0 | 500 | 0 |
| 16:1 | 500 | 31.3 |
| 16:2 | 500 | 62.5 |
| 16:4 | 500 | 125 |
| 16:8 | 500 | 250 |
| 16:16 | 500 | 500 |

(Example 10) Evaluation of Infection to T Cells Via an Antibody

First, 293T cells were seeded in a collagen coated 6-well plate so as to be present in the number of $3\times10^6$ cells and cultured in Advanced DMEM culture medium (containing 2× GlutaMAX and 10% FBS) overnight. On the following day, the culture medium was exchanged with 2 mL of Advanced DMEM culture medium (containing 2×GlutaMAX, 2% FBS (ultra-low IgG), 10 mM HEPES). Using Lipofectamine 3000 Reagent, CSIV-CMV-Venus (2.5 μg), pLenti-P3A (2.5 μg), pLenti-P3B (2.5 μg) and pVSV-G (0.625 μg); or pVSV-G (0.625 μg), 0.625 μg of pCI-SP-PA6d-GS2-VSV-G or pVSV-G, and pCI-SP-PL6d-GS2-VSV-G (0.625 gig) were transfected. Four hours after transfection, the medium was exchanged with 12 mL of Advanced DMEM culture medium (containing 2× GlutaMAX, 2% FBS (ultra-low IgG) and 10 mM HEPES) and culture was carried out for two days to prepare a lentiviral vector. The lentiviral vector prepared was subjected filtration by a 0.8 μm-filter to obtain a viral supernatant stock solution. The stock solution (10 μL) was added in a 24-well plate where 293T cells were seeded in the number of $5 \times 10^5$ cells and culture was carried out overnight in 2 mL Advanced DMEM culture medium (containing 2× GlutaMAX and 2% FBS) for infection. On the following day, the medium was exchanged. Five days after infection, cells were removed by Accumax, strained with DRAQ7 (BioStatus Limited) and analyzed by a flow cytometer. Titer (TU/ml) was calculated in accordance with the expression:

Number of cells at the time of infection $(5 \times 10^5) \times$ living cells Venus positive/total number of living cells.

The results are shown in FIG. 9.

PBMC ($1 \times 10^6$ cells) were reacted with an anti-human CD3 antibody, an anti-human CD8a antibody, an anti-human CD11a antibody or an anti-human CD19 antibody (BioLegend) present in a concentration of 1.0 μg/ml in accordance with a customary method; excessive antibody was sufficiently removed by washing with PBS; and infection was carried out by using 1 mL of the viral supernatant stock solution at 37° C. for 30 minutes. The virus solution was centrifugally removed, the cells were cultured in Advanced RPMI1640 (containing 2% FBS (ultra-low IgG), IL-2 (600 U/mL) and anti-human CD3 antibody (30 ng/mL)) for 4 days. The cells, with which an APC anti-human CD3 antibody and a Brilliant Violet 421 anti-human CD19 antibody were reacted in accordance with a customary method, were stained with a propidium iodide solution and analyzed by a flow cytometer. CD3 positive and CD19 negative cells were regarded as T cells and the proportion (%) of Venus positive T cells in living T cells was calculated. The results are shown in FIG. 9. When pCI-SP-PA6d-GS2-VSV-G was used, the efficiency of infection of T cell was improved via CD3, CD8a or CD11a, which are presumably expressed on the T cell surface, and an anti-human CD3 antibody, anti-human CD8a antibody or anti-human CD11a antibody. The efficiency of infection with pCI-SP-PL6d-GS2-VSV-G is higher than that with pVSV-G; however, improvement in efficiency of infection is not as high as that that with pCI-SP-PA6d-GS2-VSV-G. Since the binding region to an antibody differs between PA and PL, there is a possibility that the difference may influence the efficiency of infection via an antibody.

(Example 11) Evaluation of Infection to B Cells with a Retrovirus Having a Chimeric Envelope Protein (Retrovirus Except Lentivirus)

GP293 cells were seeded on a collagen coated 12-well plate so as to be present in the number of $1.5 \times 10^6$ cells and cultured in Advanced DMEM culture medium (containing 2× GlutaMAX, 10 mM HEPES, and 10% FBS) overnight. On the following day, the culture medium was exchanged with 1 mL of Advanced DMEM culture medium (containing 2× GlutaMAX, 10 mM HEPES and 10% FBS (ultra-low IgG)). Using Lipofectamine 3000 Reagent, pMSCV-bact-Venus-wpre (2 μg), pVSV-G (0.5 μg) or pVSV-G (0.5 μg); pCI-SP-PA6d-GS2-VSV-G (0.5 μg) or pVSV-G (0.5 μg); and pCI-SP-PL6d-GS2-VSV-G (0.5 μg) were transfected. Four hours after transfection, the medium was exchanged with 5 mL of Advanced DMEM culture medium (containing 2× GlutaMAX, 10% FBS or 10%/o FBS (ultra-low IgG)) and culture was carried out for two days to prepare a retroviral vector. The retroviral vector prepared was subjected filtration by a 0.8 μm-filter to obtain a viral supernatant stock solution. The stock solution (20 μL) was added in a 24-well plate where 293T cells were seeded in the number of $5.0 \times 10^5$ cells and culture was carried out overnight in 2 mL Advanced DMEM culture medium (containing 2× GlutaMAX and 2% FBS) for infection. On the following day, the medium was exchanged. Five days after infection, cells were removed by Accumax, stained with a propidium iodide solution and analyzed by a flow cytometer. Titer (TU/ml) was calculated in accordance with the expression:

Number of cells at the time of infection $(5 \times 10^5) \times$ living cells Venus positive/total number of living cells.

The results are shown in FIG. 10.

Frozen B cells were thawed and centrifuged. B cells (8000 cells) were infected by using a viral supernatant stock solution (1 mL). Two hours later, centrifugation was carried out and B cells were seeded on feeder cells (h40LB seeded in a 24-well plate so as to be present in the number of $1 \times 10^5$ cells on the previous day) and cultured in Advanced RPMI1640 (containing 2% FBS (ultra-low IgG), IL-21 (10 ng/mL), IL-2 (25 U/mL)). Five days later, cells were removed by Accutase and centrifuged. The cells, with which Alexa Fluor 647 anti-human CD19 antibody and Brilliant Violet 421 anti-mouse H-2Kd antibody were reacted in accordance with a customary method, were stained with a propidium iodide solution and analyzed by a flow cytometer. CD19 positive cells and mouse H-2Kd negative cells were regarded as B cells and the proportion (%) of Venus positive B cells in living B cells was calculated. The results are shown in FIG. 10. In the retrovirus except lentivirus, the efficiency of infection of B cells is lower than that of lentivirus, the efficiency of infection when the expression vector for the chimeric envelope protein was used, is improved compared to the case of using pVSV-G. When the expression vector for the chimeric envelope protein was used, if FBS (ultra-low IgG) was used, both titer and efficiency of infection of B cells are improved.

(Example 12) Evaluation of Infection of B Cells with Concentrated Lentivirus

Lentiviral supernatant stock solutions were prepared in the same manner as in Example 6. The stock solutions (20 mL) were centrifuged at 42,200×g and 4° C. for 2 hours. Individual precipitates were each suspended in 1 mL of Advanced RPMI1640 (containing IL-4 (50 ng/mL), IL-2 (25 U/mL), sCD40L (400 ng/mL), sBAFF (100 ng/mL), 2.5 μg/mL of ODN 2006 (Milteny Biotech)) to prepare concentrated lentiviral solutions. Each (1 μL) of the concentrated lentiviral solutions was taken and added in 293T cells seeded in a 24-well plate so as to be present in the number of $2 \times 10^5$ and infected overnight. On the following day, the medium was exchanged. Two days after infection, cells were removed by Accumax (Innovative Cell Technologies), stained with a propidium iodide solution (SIGMA) and analyzed by a flow cytometer. Titer (TU/ml) was calculated in accordance with the expression:

Number of cells at the time of infection $(2\times10^5)\times$ living cells Venus positive/total number of living cells.

The evaluation results on the relationship between the VSV-G vector concentration and the titer are shown in FIG. 11. Fresh B cells were centrifuged to obtain $1\times10^5$ cells, which were infected by using 1 mL of the concentrated lentiviral solution. Six hours later, centrifugation was carried out and the B cells were seeded on feeder cells (h40LB seeded in a 6-well plate so as to be present in the number of $5\times10^5$ cells on the previous day) and cultured in Advanced RPMI1640 (containing 2% FBS (ultra-low IgG), IL-4 (50 ng/mL) and IL-2 (25 U/mL)). Two days later, the culture medium was exchanged for Advanced RPMI 1640 (containing 2% FBS (ultra-low IgG), IL-21 (10 ng/mL) and IL-2 (25 U/mL)) and continued to culture. Two days later, the cells were removed by Accutase and centrifuged. The cells, with which Alexa Fluor 647 anti-human CD19 antibody was reacted in accordance with a customary method, were stained with a propidium iodide solution and analyzed by a flow cytometer. Human CD19 positive cells were regarded as B cells and the proportion (%) of Venus positive B cells in living B cells was calculated (FIG. 11). The results are shown in FIG. 11. The efficiency of infection of B cells can be improved by using Fresh B cells, concentrated lentivirus and stimulation from a TOLL-like receptor in combination. Note that fresh B cells were prepared without adding an antibody against the B cells. Even if an antibody is not separately added, B cells can be efficiently infected with a viral vector by using the expression vector for the chimeric envelope protein via BCR on B cells.

(Example 13) Evaluation of Infection to Mesenchymal Stem Cells (MSC) Via Antibody First 293T cells were seeded on a collagen coated 6-well plate so as to be present in the number of $3\times10^6$ cells and cultured in Advanced DMEM culture medium (containing 2× GlutaMAX and 10% FBS), overnight. On the following day, the culture medium was exchanged with 2 mL of Advanced DMEM culture medium (containing 2× GlutaMAX 2%, FBS (ultra-low IgG) and 10 mM HEPES). Using Lipofectamine 3000 Reagent, CSIV-CMV-Venus (2.5 µg), pLenti-P3A (2.5 µg), pLenti-P3B (2.5 µg), pVSV-G (0.625 µg) and pCI-SP-PA6d-GS2-VSV-G (0.625 µg) were transfected. Four hours from transfection, the medium was exchanged with 12 mL of Advanced DMEM culture medium (containing 2× GlutaMAX, 2% FBS (ultra-low IgG) and 10 mM HEPES) and culture was carried out for two days to prepare a lentiviral vector. The lentiviral vector prepared was subjected filtration by a 0.8 µm-filter to obtain a viral supernatant stock solution. Human bone marrow MSC ($5\times10^5$ cells) (PromoCell GmbH) cultured in Advanced DMEM culture medium (containing 2× GlutaMAX and 2% FBS) were reacted with an anti-human CD90 antibody (BioLegend) in a concentration of 1.0 µg/ml in accordance with a customary method; and excessive antibody was sufficiently removed by washing with PBS: and infection was carried out by using 2 mL of the viral supernatant stock solution at 37° C. for one hour. The virus solution was centrifugally removed, the cells were seeded in a 24-well plate with Advanced DMEM (containing 2× GlutaMAX and 2% FBS (ultra-low IgG)). On the following day, the medium was exchanged. Three days after infection, cells were removed by Accumax, strained with DRAQ7 and analyzed by a flow cytometer. The proportion (%) of Venus positive cells in the living MSC was calculated. The results are shown in FIG. 12. When anti CD19 antibody against CD90 expressed on MSC cells was added and infection was carried out, efficiency of infection was improved compared to the case of infection without adding the antibody.

The invention claimed is:

1. A method for producing a transgenic cell, comprising:
(a) contacting, in vitro, an antigen of a target cell with an antibody specific to the target cell;
and then contacting, in vitro:
(i) a virus comprising: a chimeric protein of an antibody-binding protein and a vesicular stomatitis virus G (VSV-G) protein; and a foreign gene, with
(ii) the antibody specific to the target cell that is in contact with the antigen of the target cell, and/or,
(b) contacting, in vitro:
(i) the virus comprising: the chimeric protein of the antibody-binding protein and the vesicular stomatitis virus G (VSV-G) protein; and the foreign gene, with
(ii) a membrane antibody of a B cell, to infect the target cell with the virus.

2. The method for producing a transgenic cell according to claim 1, wherein the antibody-binding protein comprises either one or both of an IgG-binding domain of protein A and an IgG-binding domain of protein L.

3. The method for producing a transgenic cell according to claim 2, wherein the antibody-binding protein comprises 3 or more IgG-binding domains of protein A.

4. The method for producing a transgenic cell according to claim 2, wherein the antibody-binding protein comprises 3 or more IgG-binding domains of protein L.

5. The method for producing a transgenic cell according to claim 1, wherein, in the chimeric protein, the antibody-binding protein is present at the N-terminal side of the vesicular stomatitis virus G (VSV-G) protein.

6. The method for producing a transgenic cell according to claim 1, wherein the virus is a retrovirus.

7. The method for producing a transgenic cell according to claim 6, wherein the retrovirus is a lentivirus.

8. The method for producing a transgenic cell according to claim 1, wherein the target cell is at least one of a human primary cell, a human induced pluripotent stem cell (iPS cell), a human embryonic stem cell (ES cell), a human mesenchymal stem cell, and cells differentiated and induced from said cells.

9. The method for producing a transgenic cell according to claim 1, wherein the target cell is a peripheral blood mononuclear cell.

10. The method for producing a transgenic cell according to claim 1, wherein the target cell is human B cell, human T cell or a human mesenchymal stem cell.

11. The method for producing a transgenic cell according to claim 1, wherein the target cell is human T cell; and the antibody specific to the target cell is at least one selected from an anti-human CD3 antibody, an anti-human CD8a antibody and an anti-human CD11a antibody.

12. The method for producing a transgenic cell according to claim 1, wherein the target cell is human B cell; and the virus is contacted with the target cell in vitro in the presence of at least one stimulus selected from a stimulus via IL-4, ODN 2006 and CD40 receptors and a stimulus via a BAFF receptor.

13. The method for producing a transgenic cell according to claim 1, wherein the target cell is a human mesenchymal stem cell; and the antibody specific to the target cell is an anti-human CD90 antibody.

14. The method for producing a transgenic cell according to claim 1, wherein the virus comprising a chimeric protein of an antibody-binding protein and a vesicular stomatitis virus G (VSV-G) protein comprises vesicular stomatitis virus G (VSV-G) protein in addition to the chimeric protein.

15. The method for producing a transgenic cell according to claim 14, wherein a molar ratio of the chimeric protein and the vesicular stomatitis virus G (VSV-G) protein in the virus falls within a range of 1:1 to 1:512.

16. The method for producing a transgenic cell according to claim 1, wherein the virus comprising a chimeric protein of an antibody-binding protein and a vesicular stomatitis virus G (VSV-G) protein is produced by using a plasmid vector which contains a nucleotide sequence encoding the chimeric protein of an antibody-binding protein and a vesicular stomatitis virus G (VSV-G) protein, in combination with a plasmid vector which does not comprise a nucleotide sequence encoding the antibody-binding protein and comprises a nucleotide sequence encoding the vesicular stomatitis virus G (VSV-G) protein.

17. The method for producing a transgenic cell according to claim 16, wherein a mass ratio of the plasmid vector which does not comprise a nucleotide sequence encoding the antibody-binding protein and comprises a nucleotide sequence encoding the vesicular stomatitis virus G (VSV-G) protein, and a plasmid vector which comprises a nucleotide sequence encoding the chimeric protein of an antibody-binding protein and a vesicular stomatitis virus G (VSV-G) protein falls within a range of 64:1 to 64:256.

* * * * *